United States Patent [19]

Gammill

[11] 4,434,295
[45] Feb. 28, 1984

[54] ANTI-ATHEROSCLEROTIC 6,7-DIHYDRO-7,7-DISUBSTITUTED-KHELLIN ANALOGS

[75] Inventor: Ronald B. Gammill, Portage, Mich.

[73] Assignee: The Upjohn Company, Kalamazoo, Mich.

[21] Appl. No.: 378,701

[22] Filed: May 17, 1982

[51] Int. Cl.$^3$ .......................................... C07D 311/78
[52] U.S. Cl. ................................ 549/344; 549/387;
549/332; 549/331; 549/88; 549/60; 549/13;
549/9; 548/526; 548/409; 548/201; 548/146;
546/270; 546/256; 546/197; 546/187; 546/17;
546/191; 544/378; 544/357; 544/150; 544/96;
544/60
[58] Field of Search ................ 549/387, 60, 331, 332,
549/344, 88, 9, 13; 548/409, 146, 201, 526;
546/17, 197, 187, 256, 270, 191; 544/68, 96,
150, 378, 357; 260/239 AR, 239 B, 239 BC

[56] References Cited

U.S. PATENT DOCUMENTS

| 2,680,119 | 6/1954 | Robertson et al. | 260/345.2 |
|---|---|---|---|
| 4,284,569 | 8/1981 | Gammill | 260/345.2 |

OTHER PUBLICATIONS

Abu-Shady, H., Experiments with Khellin VII., UAR J. Pharm. Sci., 11:283–288, (1970).
Abu-Shady, H., et al., Experiments with Khellin-VIII., J. Pharm. Belg., 33:397–399, (1978).
Anrep, G. V., et al., Therapeutic Uses of Khellin, The Lancet, pp. 557–558, Apr. 26, 1947.
Anrep, G. V., et al., The Coronary Vasodilator Action of Khellin, Amer. Heart J., 37:531–542, (1949).
Apffel, C. A., Die Zytostatische Wirkung von Chinonen und Ihren Derivaten, Deut. Med. Wochschr., 80:414–416, (1955).
Aubertin, E., La Khelline, agent de relachement de la musculature lisse. J. Med. Bordeaux, 127:821–823, (1950).
Baytop, O. T., Khellin'in Yer Solucanlarina Tesiri Hakkinda, Folia Pharm. (Turkey), 1:48–49, (1949).
Best, M. M., et al., Effects of Dioxyline Phosphate and Enteric-Coated Khellin on Coronary Artery Insufficiency, Amer. J. Med. Sci. 222:35–39, (1951).
Chen, G., et al., The Central Nervous Depressive Effect of Khellin, Proc. Soc. Expetl. Biol. Med., 78:305–307, (1951).
Colombo, G., et al., Sulla attivita di alcune sostanze del gruppo della Kellina sulla motilita ureterale—in vitro—, Arch. Sci. Med. 97:71–81, (1954).
Day, C. E., et al., Utility of a Selected Line (SEA) of the Japanese Quail for the Discovery of New Anti-Atherosclerosis Drugs, Laboratory Animal Science, 27:817–821, (1977).
Eaton, R. P., High Density Lipoprotein—Key to Anti--Atherogenesis, J. Chron. Dis., 31:131–135, (1978).
Haust, M. D., Reaction Patterns of Intimal Mesenchyme to Injury, and Repair in Atherosclerosis, Adv. Exp. Med. Biol., 43:35–57, (1974).
Huttrer, C. P., et al., The Chemistry and Physiological Action of Khellin and Related Products, Chem. Revs., 48:543–579, (1951).
Jordan, H., Cardiovasculare Wirkungen Intravenoser Khellin-Injektionen, Arzneimittel-Forsch 8:141–143, (1958).
Jordan, H., Cardiovasculare Wirkungen Intravenoser Khellin-Injektionen, Arzneimittel-Forsch, 7:82–85, (1957).
LaBarre, J., et al., Action protectrice de la khelline vis-a-vis de pulcere gastrique experimental provoque, chez le chien, par l'administration de cinchophene, Compt. Rend. Soc. Biol., 150:598–599, (1956).
LaBarre, J., et al., A propos de l'action inhibitrice de la khelline dans l'ulcere gastrique experimental provoque par administration journaliere de phenylbutazone, Compt. Rend. Soc. Biol., 150:1806–1807, (1956).
Lian, C., et al., Etude Experimentale et Clinique de la Khelline, Acta, Cardiol. (Brussels), 5:373–388, (1950).
Montorsi, W., et al., Sur L'Activite de Certaines Substances du Groupe de la Khelline, Presse Med., 63:81, (1955).
Musante, C., et al., Furil E. Isossazol-Furo-Cromoni e Derivati, Pharmaco. (Pavie), Ed. Sci., 15:81–94, (1960).
Mustafa, A., et al., Experiments with Furochromones, Synthesis of Ammiol and Khellol, J. Org., Chem., 26:886–890, (1961).
Mustafa, A., Furopyrans and Furopyrones, John Wiley and Sons, Inc., N.Y., (1967), pp. 102–159, (Chapter III: Furochromones).
Osher, H. L., et al., Khellin in the Treatment of Angina Pectoris, New England J. Med., 244:315–321, (1951).
Raymond-Hamet, M., Compt. Rend., 238:1624–1626, (1954).
Samaan, K., et al., The Response of the Heart to Visammin and to Khellinin, J. Pharm. Pharmacol., 1:538–544, (1949).
Samaan, K., et al., The Existence in Ammi Visnaga of a Cardiac Depressant Principle Visammin and a Cardiac Stimulant Glycoside Khellinin, J. Roy. Egypt Med. Assoc., 33:953–960, (1950).
Schonberg, A., et al., Khellin and Allied Compounds, JACS 72:1611–1617, (1950).
Schonberg, et al., Furo–Chromones and -Coumarins. XIV. JACS 77:5439–5440, (1955).
Schur, P. E., High Volume Screening Procedure for Hypobetalipoproteinemia Activity in Rats, Adv. Exp. Med. Biol. 67: Atherosclerotic Drug Discovery, pp. 215–229, Plenum Press, (1975).
Silber, E. N., The Effect of Khellin on Cardio-Pulmonary Function in Chronic Pulmonary Disease, published in 1951.
Swayne, V. R., et al., Spermicidal Action of Khellin, Amer. J. Pharm., 125:295–298, (1953).

*Primary Examiner*—Nicky Chan
*Attorney, Agent, or Firm*—Lawrence T. Welch

[57] ABSTRACT

The present specification provides novel analogs of khellin. These analogs are all useful as antiatherosclerotic agents. Particularly, the present specification provides 4-methoxy, 9-methoxy, or 4,9-dimethoxy-6,7-dihydro-7,7-disubstituted-5H-furo[3,2-g][1]benzopyran-5-ones.

14 Claims, No Drawings

ANTI-ATHEROSCLEROTIC 6,7-DIHYDRO-7,7-DISUBSTITUTED-KHELLIN ANALOGS

DESCRIPTION

1. BACKGROUND OF THE INVENTION

The present specification provides novel compositions of matter and novel methods of their preparation.

The present specification particularly relates to novel analogs of a known pharmacological agent, khellin, also known as "visamin," and structurally related antiatherogenic furochromones and other benzopyrans. Chemically, khellin is a furochromone. Furochromones are characterized generally by the structural formula IV. Specifically, khellin is the furochromone of formula V, and is trivially named 7-methyl-4,9-dimethoxyfurochromone. Khellin and related furochromones are naturally-occurring substances and have been used in crude form as pharmacological agents for centuries. Khellin is an extract from the plant *Ammi visnaga*. This plant grows wild in Eastern Mediterranean countries. Aside from khellin, *Ammi visnaga* is also a source of at least three other known and characterized furochromones, specifically visnagin, khellinin, and ammiol.

As indicated above, khellin exhibits a wide variety of pharmacological actions, rendering this compound a useful agent for numerous pharmacological purposes. For a comprehensive, but somewhat dated, review of the chemistry and physiological action of khellin-related products, see the reports of Huttrer, C. P., et al., Chem. Revs. 48:543–79 (1951) and Aubertin, E., J. Med. Bordeaux 127:821–823 (1950).

One principal action of khellin is its ability to induce relaxation of smooth muscle tissues. Particularly, khellin is known as a potent dilator of coronary blood vessels. This potent coronary vasodilator activity of khellin renders the compound useful in the treatment of angina pectoris and other diseases characterized by coronary artery insufficiency. For a description of the use of khellin in the treatment of such diseases, see Osher, H. L., et al., "Khellin in the Treatment of Angina Pectoris," The New England Journal of Medicine 244:315 (1951). Also the effects of enteric-coated khellin on coronary artery insufficiency is reported by Best, M. M., et al., J. Med. Sci. 222:35–9 (1951). The ability of khellin to relax smooth muscle also extends to gastrointestinal smooth muscle where khellin has been demonstrated to inhibit peristalsis, thus indicating antidiarrhetic potential. See Raymond-Hamet, M., Compt. Rend. 238:1624–6 (1954). Khellin may also be useful for the treatment of gastrointestinal disorders exhibiting a spasmotic component, as suggested by Anrep, G. V., et al., Amer. Heart J. 37:531–542 (1949). Further the antispasmotic effects of khellin on the urethra is reported by Colombo, G., et al., Arch. Sci. Med. 97:71 (1954) and Montorsi, W., et al., Presse Med. 63:81 (1955).

The antispasmotic action of khellin also extends to bronchial smooth muscle, rendering khellin useful in the treatment of asthma and other hypoxic pulmonary diseases. In this regard, see Silber, E. N., et al., "The Effect of Khellin on Cardio-Pulmonary Function in Chronic Pulmonary Disease," published in 1951; Anrep, G. V., et al., "Therapeutic Uses of Khellin," The Lancet, Apr. 26, 1947, pages 557–8.

Khellin has also been reported to exert a hypotensive effect in humans by Jordan, H., Arzneimittel-Forsch 8:141-3 (1958), and 7:82-5 (1957). An additional account of the hypotensive effect of khellin is provided by Lian, C., et al., Acta. Cardiol. (Brussels) 5:373–88 (1950). With respect to overall cardiac effects, however, khellin has been reported to exert a cardiac depressive activity. In this regard see Samaan, K., et al., J. Roy. Egypt Med. Assoc. 33:953 (1950) and J. Pharm. Pharmacol. 1:538–44 (1949).

In addition to its effect on gastrointestinal smooth muscle reported above, khellin is also known as a gastric antisecretory and antiulcer agent. In this regard, the gastric antisecretory activity of khellin is reported by LaBarre, J., Compt. Rend. Soc. Biol. 150:1806$\alpha$7 (1956) and 150:598–9 (1956).

Numerous other miscellaneous properties of khellin are also reported. For an account of its anthelminic activity see Baytop, O. T., Folia, Pharm. (Turkey) 1:48–9 (1949). For an account of the CNS depressant activity of khellin see Chen, G., Proc. Soc. Expetl. Biol. Med. 78:305–7 (1951). For an account of the cytostatic activity of khellin see Apffel, C. A., Deut. Med. Worschr. 80:414–16 (1955). Finally, the spermacidal action of khellin is reported by Swayne, V. R., et al., Amer. J. Pharm. 125:295–8 (1953).

Khellin and numerous chemically related furochromones (and derivatives thereof) are also useful in treatment and prevention of atherosclerosis by methods described in U.S. Pat. No. 4,284,569.

Atherosclerosis in mammals is a disease characterized by the deposition of atherosclerotic plaque on arterial walls. While atherosclerosis exhibits many varied forms and consequences, typical consequences of atherosclerotic diseases include angina pectoris, myocardial infarction, stroke and transient cerebral ischemic attacks. Other forms of atherosclerotic diseases include certain peripheral vascular diseases and other ischemias (e.g., bowel and renal).

Medical science now recognizes that certain forms of atherosclerosis may be preventable or reversible. Agents capable of preventing or reversing atherosclerosis are characterized as exhibiting antiatherosclerotic activity. Since serum lipids have a recognized association with atherogenesis, an important class of antiatherosclerotic agents are those with serum lipid-modifying effects. Serum lipids implicated in atherogenesis include serum cholesterol, serum triglycerides, and serum lipoproteins.

With respect to serum lipoproteins, at least three different classes of these substances have been characterized: high density lipoproteins (HDL's), low density lipoproteins (LDL's), and very low density lipoproteins (VLDL's). HDL's are often referred to as alphalipoproteins, while LDL's and VLDL's are referred to as betalipoproteins. The enhancement to HDL levels (hyperalpha-lipoproteinemic activity) is postulated to have direct antiatherosclerotic effects. See Eaton, R. P., J. Chron. Dis. 31:131–135 (1978). In contrast, agents which reduce serum LDL's and serum VLDL's (hypobetalipoproteinemic agents) are also associated with antiatherogenic effects. See Haust, M. D., "Reaction Patterns of Intimal Mesenchyme to Injury and Repair in Atherosclerosis:," Adv. Exp. Med. Biol. 43:35–57 (1974), which postulates that serum LDL is a factor in atherosclerotic lesion formation.

Numerous animal models have been developed for assessing antiatherogenic activity. Principal among these are models for assessing hypobetalipoproteinemic activity in the rat, antiatherosclerotic activity in the Japanese quail, and lipoprotein modifying activity in the monkey. For a description of the operation of the hypobetalipoproteinemic rat model, refer to the known methods of Schurr, P. E., et al., "High Volume Screening Procedure for Hypobetalipoproteinemia Activity in Rats," Adv. Exp. Med. Biol. 67: Atherosclerotic Drug Discovery, pp. 215–229, Plenum Press (1975). For a description of the Japanese quail model, see Day, C. E., et al., "Utility of a Selected Line (SEA) of the Japanese Quail (Coturnix coturnix japonica) for the Discovery of New Anti-Atherosclerosis Drugs," Laboratory Animal Science 27:817–821 (1977).

A suitable primate model for assessing antiatherosclerotic activity of chemical compounds is found in the cynomolgus monkey. In these animals base-line values for VLDL's, LDL's, and HDL's can be determined by controlling diet over a period of several weeks and sampling plasma daily. After establishing control values, the effects of drug treatment are assessed by administering by gavage with a predetermined series of doses of test compounds for a similar period (e.g., two weeks).

The khellin, the khellin-related products of *Ammi visnaga*, and related furochromones (and derivatives) described in U.S. Pat. No. 4,284,569 are all characterized by pronounced antiatherogenic activity, rendering these compounds useful in the treatment and prophylaxis of atheroscherosis, atherogenic hyperlipoproteinemia (i.e., hypobetalipoproteinemia) and atherogenic hypolipoproteinemia (i.e., hypoalphalipoproteinemia), and the untoward consequences thereof. These compounds exhibit this useful pharmacological activity in both mammalian and non-mammalian species, including humans.

The patients susceptible to the development of atherosclerotic diseases and the untoward consequences thereof are particularly those physically asymptomatic patients manifesting one or more risk factors known to predispose one to disease development. Such risk factors are high serum cholesterol and serum triglycerides, hypertension, obesity, diabetes, and genetic predisposition. Patients manifesting two or more risk factors are deemed to be especially susceptible to atherosclerotic diseases. These khellin-related materials all exhibit pronounced oral pharmacologic activity. Accordingly, in using these compounds for the treatment of atherosclerosis, an oral route of administration, either by conventional oral dosage forms or by mixture with food, represents the preferred method of their systemic administration. Alternatively, however, these compounds may be administered by other convenient routes of administration whereby systemic activity is obtained. These other routes of administration would, accordingly, include rectal, vaginal, subcutaneous, intravenous, and like routes.

In humans, the preferred route of administration is oral, in the form of capsules or tablets containing the drug.

The patient or animal being treated must be given periodic doses of the drug in amounts effective to reduce atherogenic serum lipoproteins (e.g., betalipoproteins) or selectively enhance levels of antiatherogenic serum lipoproteins (e.g., enhancing alphalipoprotein levels, while suppressing, or at least unaffecting, betalipoprotein levels). Such effective dosages are readily determined by methods known in the art. For example, small daily doses of the drug (e.g., 50–100 mg) may be administered initially with higher succeeding doses until levels of atherogenic or antiatherogenic serum lipoproteins are favorably affected. By this regimen, a compound is administered initially at doses as low as about 50 mg per patient per day, with increasing doses up to about 200 mg per patient per day. In the event the antiatherogenic response in a patient being treated at a dose of 200 mg per day is insufficient, higher doses are also utilized to the extent tolerance permits further increases in dose.

While the preferred dosage regimen is with single daily dosing of patients, also preferred for obtaining more uniform serum levels of drug are multiple dosages per day (e.g., up to 4–6 times daily). Accordingly, when 4 daily doses of drug are to be administered, each such dose may be about 50 mg per patient per dose (200–300 mg per patient per dose), or higher depending on tolerance.

Similar doses are employed in non-human mammals, e.g., 1–5 mg/kg/day.

4,9-Dimethoxyfurochromones are known in the art. Such known compounds include 7-ethyl, 7-phenyl, 7-propyl, and 7-ethoxycarbonyl analogs described by Schonberg, A., et. al., JACS 72:1611–17 (1950); 7-γ-pyridyl analogs, described by Schonberg, A., JACS 77:5439 (1955); 7-furanyl analogs, described by Musante, C., et al., Pharmaco. (Pavie) Ed. Sci. 15:81–94 (1960); 7-carboxyaldehyde analogs, described by Mustafa, A., et al., J. Org. Chem. 26:886 (1961). Also, 6-substituted-4,9-dimethoxyfurochromones are known. See, for example, the compounds described by Abu-Shady, H., UAR J. Pharm. Sci. 11:283 (1970).

4-Methoxy-7-aminomethylenefurochromones are also known in the art. See Abu-Shady, H., et al, J. Pharm. Belg. 33:397 (1978).

A wide variety of antiatherosclerotic furochromones are described in U.S. Pat. No. 4,284,569.

2. PRIOR ART

Extensive pharmacological uses for khellin and related substances are known, as indicated above. Khellin analogs are also known in the art, as indicated above. See especially U.S. Pat. No. 4,284,569 and the review by Mustafa, A., "Furopyrans and Furopyrones," John Wiley and Sons, Inc., N.Y., N.Y. (1967), pp. 102–159 (Chapter III: Furochromones). Also see U.S. Pat. No. 2,680,119 describing 6- and/or 7-substituted furochromones, i.e., alkyl, alkoxyalkyl and phenylalkyl substituted compounds.

SUMMARY OF THE INVENTION

The present invention particularly provides:
(1) A dihydrofurochromone of formula I
wherein $R_1$ and $R_2$, being the same or different, are individually:
    (a) $C_1$–$C_6$ alkyl,
    (b) trifluoromethyl,
    (c) $C_5$–$C_{10}$ cycloalkyl with the proviso that the cycloalkyl ring is $C_5$–$C_7$,
    (d) $C_2$–$C_8$ alkylaminoalkyl,
    (e) $C_2$–$C_8$ alkoxyalkyl,
    (f) $C_2$–$C_8$ alkylthioalkyl,
    (g) $C_2$–$C_8$ alkylsulfinylalkyl,
    (h) $C_2$–$C_8$ alkylsulfonylalkyl,
    (i) $C_7$–$C_{12}$ phenoxyalkyl optionally substituted on the phenyl ring by one, 2, or 3,
        (i) hydroxy,
        (ii) $C_1$–$C_3$ alkoxy,
        (iii) $C_1$–$C_3$ alkyl,
        (iv) trifluoromethyl, (v) halo which is fluoro, chloro, or bromo, with the proviso that not more than two such substituents are other than alkyl,
(j) $C_7$-$C_{12}$ phenylthioalkyl optionally substituted on the phenyl ring by one, 2, or 3.
  (i) hydroxy,
  (ii) $C_1$-$C_3$ alkoxy,
  (iii) $C_1$-$C_3$ alkyl,
  (iv) trifluoromethyl,
  (v) halo which is fluoro, chloro, or bromo, with the proviso that not more than two such substituents are other than alkyl,
(k) phenyl optionally substituted by one, 2, or 3,
  (i) hydroxy,
  (ii) $C_1$-$C_3$ alkoxy,
  (iii) $C_1$-$C_3$ alkyl,
  (iv) trifluoromethyl,
  (v) halo which is fluoro, chloro, or bromo, with the proviso that not more than two such substituents are other than alkyl,
(l) aralkyl optionally substituted on the aromatic ring by one, 2, or 3,
  (i) hydroxy,
  (ii) $C_1$-$C_3$ alkoxy,
  (iii) $C_1$-$C_3$ alkyl,
  (iv) trifluoromethyl,
  (v) halo which is fluoro, chloro, or bromo, with the proviso that not more than two such substituents are other than alkyl,
(m) 2- or 3-furanyl optionally substituted by
  (i) hydroxy,
  (ii) $C_1$-$C_3$ alkoxy,
  (iii) $C_1$-$C_3$ alkyl,
  (iv) trifluoromethyl,
  (v) halo which is fluoro, chloro, or bromo, with the proviso that not more than two such substituents are other than alkyl,
(n) 2- or 3-thenyl optionally substituted by
  (i) hydroxy,
  (ii) $C_1$-$C_3$ alkoxy,
  (iii) $C_1$-$C_3$ alkyl,
  (iv) trifluoromethyl,
  (v) halo which is fluoro, chloro, or bromo, with the proviso that not more than two such substituents are other than alkyl, or
(o) $-CH_2NR_8R_9$ wherein $R_8$ and $R_9$, being the same or different, are individually,
  (i) hydrogen,
  (ii) $C_1$-$C_8$ alkyl,
  (iii) $C_5$-$C_{10}$ cycloalkyl,
  (iv) $C_7$-$C_{12}$ aralkyl, or
  (v) phenyl optionally substituted by one, 2, or 3
    (a) hydroxy,
    (b) $C_1$-$C_3$ alkoxy,
    (c) $C_1$-$C_3$ alkyl,
    (d) trifluoromethyl,
    (e) halo which is fluoro, chloro, or bromo, with the proviso that not more than two such substituents are other than alkyl, or
  wherein $R_8$ and $R_9$ are taken together with the nitrogen to form a saturated or unsaturated heterocyclic amine ring consisting of from 2 to 7 carbon atoms, inclusive, and zero, one, or 2 additional hetero atoms or hetero atom groups, with the proviso that said heterocyclic amine ring contains 4 to 8 atoms in the ring, said additional hetero atoms or hetero atom groups being selected from the group consisting of oxygen, nitrogen, sulfur, —SO—, and —$SO_2$— said heterocyclic amine ring being optionally substituted by $C_1$-$C_4$ alkyl, $C_2$-$C_8$ alkylthiomethyl, $C_2$-$C_8$ alkoxymethyl, $C_1$-$C_4$ hydroxymethyl or phenyl; or wherein $R_1$ and $R_2$ are taken together and form a bivalent moiety which is:
(a) $-CH_2-(CH_2)_a-CH_2-$ wherein the integer "a" is zero to 5;
(b) $-CH_2-(CH_2)_b-X-(CH_2)_c-CH_2-$
wherein the integer "b" is zero and the integer "c" is zero, one, 2, or 3 or the integer "b" is one and the integer "c" is zero, one, or 2, and wherein X is oxa (—O—), thia (—S—), or —$N(R_{10})$— wherein $R_{10}$ is
  (i) hydrogen,
  (ii) $C_1$-$C_8$ alkyl,
  (iii) $C_5$-$C_{10}$ cycloalkyl,
  (iv) $C_7$-$C_{12}$ aralkyl, or
  (v) phenyl optionally substituted by one, 2, or 3
    (a) hydroxy,
    (b) $C_1$-$C_3$ alkoxy,
    (c) $C_1$-$C_3$ alkyl,
    (d) trifluoromethyl,
    (e) halo which is fluoro, chloro, or bromo, with the proviso that not more than two such substituents are other than alkyl;

wherein $R_3$ is hydrogen or $C_1$-$C_4$ alkoxy and $R_4$ is hydrogen or $C_1$-$C_4$ alkoxy, with the provisos that one of $R_3$ and $R_4$ is hydrogen only when the other is other than hydrogen and $R_3$ and $R_4$ are the same or different.

(2) A dihydrofurochromone selected from the group consisting of:
(a) 6,7-Dihydro-4,9-dimethoxy-7,7-dimethyl-5H-furo[3,2-g][1]benzopyran-5-one,
(b) 7-Ethyl-6,7-dihydro-4,9-dimethoxy-7-methyl-5H-furo[3,2-g][1]benzopyran-5-one,
(c) 7,7-Diethyl-6,7-dihydro-4,9-dimethoxy-5H-furo[3,2-g][1]benzopyran-5-one,
(d) 6,7-Dihydro-4,9-dimethoxy-7-methyl-7-phenyl-5H-furo[3,2-g][1]benzopyran-5-one,
(e) 4',9'-Dimethoxy-spiro[cyclopentane-1,7'-[7H]furo[3,2-g][1]benzopyran]-5'(6'H)-one,
(f) 4',9'-Dimethoxy-spiro[cyclohexane-1,7'-[7H]furo[3,2-g][1]benzopyran]-5'(6'H)-one,
(g) 2',3',5',6'-Tetrahydro-4,9-dimethoxy-spiro[7H]furo[3,2-g][1]benzopyran-7,4'-[4H]thiopyran]-5(6H)-one,
(h) 2',3',5',6'-Tetrahydro-4,9-dimethoxy-spiro[7H-furo[3,2-g][1]benzopyran-7,4'-[4H]thiopyran]-5(6H)-one, 1'-oxide,
(i) 2',3',5',6'-Tetrahydro-4,9-dimethoxy-spiro[7H-furo[3,2-g][1]benzopyran-7,4'-[4H]thiopyran]-5(6H)-one, 1',1'-dioxide,
(j) 6,7-Dihydro-4,9-dimethoxy-7-methyl-7-[(methylthio)-methyl]-5H-furo[3,2-g][1]benzopyran-5-one,
(k) 6,7-Dihydro-4,9-dimethoxy-7-methyl-7-[(methylthio)-methyl]-5H-furo[3,2-g][1]benzopyran-5-one, oxide,
(l) 6,7-Dihydro-4,9-dimethoxy-7-methyl-7-[(methylthio)-methyl]-5H-furo[3,2-g][1]benzopyran-5-one, dioxide, or
(m) 4,9-Dimethoxy-1'-methyl-spiro[7H-furo[3,2-g][1]benzopyran-7,4'-piperidine]-5(6'H)-one.

The carbon atom content of various hydrocarbon containing moieties is indicated by a prefix designating the minimum and maximum number of carbon atoms in the moiety, i.e., the prefix $C_i-C_j$ indicates a carbon atom content of the integer "i" to the integer "j" carbon atoms, inclusive. Thus, $C_1-C_3$ alkyl refers to alkyl of 1-3 carbon atoms, inclusive, or methyl, ethyl, propyl, and isopropyl.

With respect to the above, $C_1-C_4$ alkyl is methyl, ethyl, propyl, or butyl, including isomeric forms thereof. Similarly, $C_1-C_6$ alkyl is methyl, ethyl, propyl, butyl, pentyl, hexyl, and isomeric forms thereof.

Examples of cycloalkyl of 3 to 10 carbon atoms, inclusive, are cyclopropyl, cyclobutyl, cyclopentyl, cyclohexyl, cycloheptyl, cyclodecyl, cyclopropylmethyl, cyclobutylmethyl, cyclopentylmethyl, cyclohexylmethyl, cycloheptylmethyl, 1- or 2-cyclopropylethyl, 1- or 2-cyclobutylethyl, 1- or 2-cyclopentylethyl, 1- or 2-cyclohexylethyl, 1-, 2-, 3- or 4-methylcyclohexyl, (bicyclo[3.1.1]hept-2-yl)methyl, and 6,6-dimethyl-(bicyclo[3.1.1]hept-2-yl)methyl.

Example of alkoxyaminoalkyl are methylaminomethyl, ethylaminomethyl, propylaminomethyl, butylaminomethyl, isopropylaminomethyl, isobutylaminomethyl, tert-butylaminomethyl, pentylaminomethyl, and n-hexylaminomethyl.

Examples of $C_2-C_8$ alkoxyalkyl are methoxymethyl, ethoxymethyl, propoxymethyl, butoxymethyl, pentoxymethyl, hexoxymethyl, and heptoxymethyl.

Examples of $C_2-C_8$ alkylthioalkyl are methylthiomethyl, ethylthiomethyl, propylthiomethyl, butylthiomethyl, isopropylthiomethyl, isobutylthiomethyl, tert-butylthiomethyl, pentylthiomethyl, and n-hexylthiomethyl.

Examples of $C_2-C_8$ alkylsulfinylalkyl are methylsulfinylmethyl, ethylsulfinylmethyl, propylsulfinylmethyl, butylsulfinylmethyl, isopropylsulfinylmethyl, isobutylsulfinylmethyl, tert-butylsulfinylmethyl, pentylsulfinylmethyl, and n-hexylsulfinylmethyl.

Examples of $C_2-C_8$ alkylsulfonylalkyl are methylsulfonylmethyl, ethylsulfonylmethyl, propylsulfonylmethyl, butylsulfonylmethyl, isopropylsulfonylmethyl, isobutylsulfonylmethyl, tert-butylsulfonylmethyl, pentylsulfonylmethyl, and n-hexylsulfonylmethyl.

Example of $C_6-C_{12}$ phenoxyalkyl optionally substituted are phenoxymethyl, phenoxyethyl, phenoxypropyl, phenoxybutyl, phenoxypentyl, 1-, 2-, or 3-methylphenoxymethyl, 1-, 2-, or 3-hydroxyphenoxymethyl, 1-, 2-, or 3-methoxyphenoxymethyl, 1-, 2-, or 3-trifluoromethylphenoxymethyl, 1-, 2-, or 3-fluorophenoxymethyl, and 1-fluoro-3-methyl-phenoxymethyl.

Example of $C_6-C_{12}$ phenylthioalkyl optionally substituted are phenylthiomethyl, phenylthioethyl, phenylthiopropyl, phenylthiobutyl, phenylthiopentyl, 1-, 2-, or 3-methylphenylthiomethyl, 1-, 2-, or 3-hydroxyphenylthiomethyl, 1-, 2-, or 3-methoxyphenylthiomethyl, 1-, 2-, or 3-trifluoromethylphenylthiomethyl, 1-, 2-, or 3-fluorophenylthiomethyl, and 1-fluoro-3-methyl-phenylthiomethyl.

Example of $C_6-C_{12}$ phenyl optionally substituted are phenyl, 1-, 2-, or 3-methylphenyl, 1-, 2-, or 3-hydroxyphenyl, 1-, 2-, or 3-methoxyphenyl, 1-, 2-, or 3-trifluoromethylphenyl, 1-, 2-, or 3-fluorophenyl, and 1-fluoro-3-methylphenyl.

Examples of aralkyl of 7 to 12 carbon atoms are naphthylmethyl and naphthylethyl.

Examples of heterocyclic amines corresponding to heterocyclic amine rings are thiazolidine, 3-piperidine methanol, 2-piperidine methanol, 3-piperidine ethanol, 2-piperidine ethanol, 1-piperizinepropanol, 4-phenyl-1,2,3,6-tetrahydropyridine, 4-phenylpiperidine, proline, 3-pyrolidinol, tetrahydrofurfurylamine, 3-pyrroline, thiazolidine-4-carboxylic acid, thiomorpholine, morpholine, 2-methylpiperidine, 3-methylpiperidine, 4-methylpiperidine, N-methylpiperazine, and 1-methylhomopiperazine.

The compounds in accordance with the present invention are all useful as antiatherosclerotic agents. Thus these compounds are employed by methods known in the art for the use of khellin and related furochromones in the treatment and prevention of atherosclerosis. Accordingly, compounds of formula I are employed in humans and in nonhuman mammals at doses from about 0.1-50 mg/kg/day orally. These compounds are used orally in conventional oral dosage forms, including capsules, tablets, and pharmaceutically acceptable liquids. Other routes of administration may also be employed, utilizing equivalent dosages and the appropriate conventional dosage form for the route of administration selected. Such alternatively dosage forms include rectal, vaginal, subcutaneous, intravenous, and like routes of administration.

Compounds of formula I are also useful as food or feed additives whereby the ingestion of food or feed by the mammal being treated results in an effective oral dose of the compound.

Preferred among the compounds of formula I are those wherein at least one of $R_3$ and $R_4$ is methoxy and more preferably both are methoxy.

By virtue of the ring structure of the compounds of the present invention, these substances are named as either 4-alkoxy-, 9-alkoxy-, or 4,9-dialkoxy- (depending upon whether, respectively, $R_3$ is alkoxy and $R_4$ is hydrogen, $R_4$ is alkoxy and $R_3$ is hydrogen, or $R_3$ and $R_4$ are both alkoxy), 6,7-dihydro-7,7-disubstituted-5H-furo[3,2-g][1]benzopyran-5-ones when $R_1$ and $R_2$ are not taken together to form a spiro ring. The compounds so described by formula I are 6,7-dihydro-spiro[1,7'-[7H]furo[3,2-g][1]benzopyran]-5'(6'H)-ones.

The novel compounds disclosed in the present specification are all prepared by methods described in Chart A.

With respect to the chart, the various substituents, $R_1$, $R_2$, $R_3$ and $R_4$ are as defined above in the specification.

With respect to Chart A, the formula XXII compound is known. The preparation of this compound wherein $R_3$ or $R_4$ is methoxy or $R_3$ and $R_4$ are both methoxy is described in U.S. Pat. No. 4,284,569, where its synthesis from khellin or related compounds is described. Preferably the formula XXI compound is prepared by the methods described in Copending U.S. applications Ser. Nos. 378,686 and 378,687, both filed May 17, 1982 (the specifications of which are attached hereto as appendices A and B), by a total synthetic route.

In accordance with the procedure of Chart A, the formula XXI compound is reacted with a ketone of formula XXII wherein $R_1$ and $R_2$ are as defined above. This reaction produces the formula XXIII product, i.e., the compounds of formula I. This reaction proceeds by combining the ketone of formula XXII and the formula XXI reactant with a cyclic amine base, e.g., especially pyrrolidine, and heating for a prolonged period at elevated temperature. For example, the reaction proceeds at reflux for a period ranging from several hours to several days. Thereupon the formula XXIII product is obtained from the reaction mixture by conventional separation techniques, i.e., filtration, chromatography, and crystallization.

The sulfoxide (—SO—) and sulfone (—SO$_2$—) compounds herein are preferrably prepared from corresponding thio (—S—) compounds by oxidization. Such oxidizations are carried out by methods known in the art for the preparation of sulfoxides and sulfonyl derivatives of thio-containing compounds. For example, a useful oxidizing agent for this purpose is m-chloroperoxybenzoic acid and sodium periodate.

Thus, in accordance with the procedure of Chart A, each of the various formula I compounds provided in the present disclosure is prepared.

DESCRIPTION OF THE PREFERRED EMBODIMENTS

The preparation of the novel compounds disclosed herein is more readily understood by the operation of the following examples:

EXAMPLE 1

6,7-Dihydro-4,9-dimethoxy-7,7-dimethyl-5H-furo[3,2-g][1]benzopyran-5-one (Formula I, $R_1$ and $R_2$ are both methyl, and $R_3$ and $R_4$ are both methoxy).

Refer to Chart A.

Toluene (15 ml) and 1-(6-hydroxy-4,7-dimethoxy-5-benzofuranyl)-ethanone (6.5 g) are combined with acetone (25 ml) and pyrrolidine (0.75 ml). The resulting mixture is then heated under nitrogen to reflux for 96 hr and then allowed to cool to ambient temperature. Concentration under reduced pressure yields a dark oil which crystallizes. High pressure liquid chromatography on 350 g of silica gel eluting with ethyl acetate yields 8.4 g of title product as a yellow solid. This solid is diluted with dichloromethane and filtered through basic alumina. The filtrate is then dried and the resulting residue recrystallized from ethyl acetate in hexane to yield 3.8 g of pure title product, melting point 90°-92° C. Silica gel TLC $R_f$ is 0.21 in 25% ethyl acetate in hexane. IR absorptions (cm$^-$) are observed at 3140, 1670, 1610, 1595, 1550, 1480, 1355, 1305, 1145, 1080, and 1060. NMR absorptions (CDCl$_3$, δ) are observed at 7.55, 6.95, 4.05, 4.01, 2.72, and 1.50.

EXAMPLE 2

7-Ethyl-6,7-dihydro-4,9-dimethoxy-7-methyl-5H-furo[3,2g][1]benzopyran-5-one (Formula I, $R_1$ is methyl, $R_2$ is ethyl, and $R_3$ and $R_4$ are both methoxy).

Refer to Chart A.

Benzene (100 ml) and 1-(6-hydroxy-4,7-dimethoxy-5-benzofuranyl)ethanone (9.68 g) and 2-butanone (10 ml) are combined under a nitrogen atmosphere and pyrrolidine (1 ml) is added. The resulting mixture is then heated to reflux for 72 hr. After cooling to ambient temperature, the reaction mixture is diluted with ethyl acetate and extracted with 2 N aqueous sodium hydroxide (50 ml), 2 N hydrochloric acid (100 ml), and brine (20 ml). The organic phase is then dried over magnesium sulphate and filtered. The resulting filtrate is then concentrated under reduced pressure to a residue which is chromatographed on 330 g of silica gel, elluding with 20% ethyl acetate in hexane. Pure title product, 8.0 g of an oil, is obtained. Crystallization of the oil followed by recrystallization yields 4.04 g of pure title product, melting point 68°-71° C. Silica gel TLC $R_f$ is 0.22 in 25% ethyl acetate in hexane. IR absorptions (cm$^-$) are observed at 3180, 3140, 1685, 1615, 1590, 1550, 1350, 1300, 1140, 1080, and 1060. NMR absorptions (CDCl$_3$, δ) are observed at 7.50, 6.90, 4.04, 4.01, 2.73, 1.82, 1.45, and 1.00.

EXAMPLE 3

7,7-Diethyl-6,7-dihydro-4,9-dimethoxy-5H-furo[3,2-g][1]benzopyran-5-one (Formula I, $R_1$ and $R_2$ are both ethyl, and $R_3$ and $R_4$ are both methoxy).

Refer to Chart A.

Following the procedure of Example 1 or Example 2, 1-(6-hydroxy-4,7-dimethoxy-5-benzofuranyl)-ethanone (5.1 g) and 3-pentanone (12.8 ml) are transformed to the title product, 2.82 g of crystalline material, melting point 72°-73° C. Silica gel TLC $R_f$ is 0.24 in 25% ethyl acetate in hexane. IR absorptions (cm$^{-1}$) are observed at 3120, 3060, 1670, 1605, 1595, 1500, 1480, 1345, 1315, 1140, 1080, 1065, and 750. NMR absorptions (CDCl$_3$, δ) are observed at 7.50, 6.92, 4.07, 2.75, 1.81, and 0.98.

EXAMPLE 4

6,7-Dihydro-4,9-dimethoxy-7-methyl-7-phenyl-5H-furo[3,2-g][1]benzopyran-5-one (Formula I, $R_1$ is methyl, $R_2$ is phenyl, and $R_3$ and $R_4$ are both methoxy).

Refer to Chart A.

Following the procedure of Example 1 or Example 2, 1-(6-hydroxy-4,7-dimethoxy-5-benzofuranyl)-ethanone (5.3 g) and acetophenone (6.0 ml) are transformed to 0.5 g of crystalline title product, melting point 161°-162° C. Silica gel TLC $R_f$ is 0.10 in 25% ethyl acetate in hexane. IR absorptions (cm$^{-1}$) are observed at 3130, 1675, 1600, 1550, 1495, 1350, 1315, 1310, 1275, 1140, 1080, 1055, 770, 740, 730, and 705. NMR absorptions (CDCl$_3$, δ) are observed at 7.4, 6.84, 4.15, 3.95, 3.38, 3.04, and 1.80.

EXAMPLE 5

4′,9′-Dimethoxy-spiro[cyclopentane-1,7′-[7H]furo[3,2-g][1]benzopyran]-5′(6′H)-one (Formula I, $R_1$ and $R_2$ taken together are —(CH$_2$)$_4$—, and $R_3$ and $R_4$ are both methoxy).

Refer to Chart A.

Following the procedure of Example 1 or Example 2, 1-(6-hydroxy-4,7-dimethoxy-5-benzofuranyl)-ethanone (50 g) and cyclopentanone (29 ml) are transformed to title product, 49.2 g of a yellow solid, melting point 75°-77° C. Silica gel TLC $R_f$ is 0.32 in 25% ethyl acetate in hexane. IR absorptions (cm$^{-1}$) are observed at 3120, 3070, 1685, 1610, 1590, 1550, 1480, 1355, 1145, and 1080. NMR absorptions (CDCl$_3$, δ) are observed at 7.55, 6.93, 46.08, 4.00, 2.83, 2.30-1.50.

EXAMPLE 6

4′,9′-Dimethoxy-spiro[cyclohexane-1,7′-[7H]furo[3,2-g][1]benzopyran]-5′(6′H)-one (Formula I, $R_1$ and $R_2$ taken together are —(CH$_2$)$_5$—, and $R_3$ and $R_4$ are both methoxy).

Refer to Chart A.

Following the procedure of Example 1 or Example 2, 1-(6-hydroxy-4,7-dimethoxy-5-benzofuranyl)-ethanone (5.97 g) and cyclohexanone (3.45 ml) are transformed to pure title prouct as a pale yellow crystal (5.93 g), melting point 102°-104° C. Silica gel TLC $R_f$ is 0.30 in 25% ethyl acetate in hexane. IR absorptions (cm$^{-1}$) are observed at 3140, 3120, 1690, 1620, 1540, 1480, 1350, 1280, 1125, and 1060. NMR absorptions (CDCl$_3$, δ) are observed at 7.52, 6.92, 4.08, 2.70, 2.25-1.20.

EXAMPLE 7

2′,3′,5′,6′-Tetrahydro-4,9-dimethoxy-spiro[7H-furo[3,2-g][1]benzopyran-7,4′-[4H]thiopyran]-5(6H)-one (Formula I, $R_1$ and $R_2$ taken together are —$(CH_2)_2$—S—$(CH_2)_2$—, and $R_3$ and $R_4$ are both methoxy).

Refer to Chart A.

Following the procedure of Example 1 or Example 2, 1-(6-hydroxy-4,7-dimethoxy-5-benzofuranyl)-ethanone (10.63 g) and tetrahydrothiopyran-4-one (7.8 g) are transformed to pure title product (9.42 g), melting point 146.7°–147.9° C. Silica gel TLC $R_f$ is 0.1 L in 25% ethyl acetate in hexane. IR absorptions (cm$^{-1}$) are observed at 3140, 3120, 1685, 1620, 1535, 1475, 1350, 1125, and 1065. NMR absorptions (CDCl$_3$, δ) are observed at 7.55, 6.95, 4.10, 4.07, 3.45, 2.80, 2.72, 2.7–1.5.

EXAMPLE 8

2′,3′,5′,6′-Tetrahydro-4,9-dimethoxy-spiro[7H-furo[3,2-g][1]benzopyran-7,4′-[4H]thiopyran]-5(6H)-one, 1′-oxide and 2′,3′,5′,6′-Tetrahydro-4,9-dimethoxy-spiro[7H-furo[3,2-g][1]benzopyran-7,4′-[4H]thiopyran]-5(6H)-one, 1′,1′-dioxide (Formula I: $R_1$ and $R_2$ taken together are —$(CH_2)_2$—SO—$(CH_2)_2$— or —$(CH_2)_2$—SO$_2$—$(CH_2)_2$—, respectively, and $R_3$ and $R_4$ are both methoxy.

Refer to Chart A.

A. A solution of the title product of Example 7 (4.15 g) in a mixture of methanol and tetrahydrofuran (1:1) are diluted with water (75 ml) and then treated with sodium periodate (2.7 g). After about 30 min a precipitate appears. The reaction is then continued with stirring at ambient temperature for 12 hr and filtered. The filter cake is then washed with methanol (100 ml) and the total filtrate concentrated under reduced pressure to a residue, a mixture of title product.

B. The mixture of Part A is then combined with dichloromethane and m-chloroperoxybenzoic acid (2.1 g) and stirred for 16 hrs. Treatment with 2 normal sodium hydroxide (75 ml) is followed by stirring for 5 min and separation of phases. The organic layer is then dried over sodium sulfate and concentrated under reduced pressure to a residue. Chromatography on silica gel eluting with ethyl acetate in trichloromethane (1:1) yields 4 g of sulfone. Recrystallization from acetone and hexane (5:1) yields 3.6 g of pure title product. Silica gel TLC $R_f$ is 0.33 in ethyl acetate. IR absorptions (cm$^{-1}$) are observed at 3160, 3120, 3080, 1685, 1605, 1595, 1555, 1475, 1315, 1295, 1135, 1100, 1080, and 1070. NMR absorptions (CDCl$_3$, δ) are observed at 7.61, 6.99, 4.18, 4.13, 3.8–2.9, 2.78, and 2.75–2.2.

EXAMPLE 9

6,7-Dihydro-4,9-dimethoxy-7-methyl-7-[(methylthio)methyl]-5H-furo[3,2-g][1]benzopyran-5-one (Formula I, $R_1$ is methyl, $R_2$ is methylthiomethyl, and $R_3$ and $R_4$ are both methoxy).

Refer to Chart A.

Following the procedure of Example 1 or Example 2, 1-(6-hydroxy-4,7-dimethoxy-5-benzofuranyl)-ethanone (8.33 g) and thiomethyl acetone (5.5 ml) are transformed to 7.5 g of crystalline title product. Recrystallization from methyl acetate in hexane yields pure crystalline product, melting point 64°–66° C. Silica gel TLC $R_f$ is 0.40 in 50% ethyl acetate in hexane. IR absorptions (cm$^{-1}$) are observed at 3160, 3120, 3060, 1680, 1615, 1590, 1545, 1475, 1305, 1160, 1150, 1140, 1080, and 1065. NMR absorptions (CDCl$_3$, δ) are observed at 7.55, 6.95, 4.05, 4.01, 3.16, 2.93, 2.60, 2.26, and 1.58.

EXAMPLE 10

6,7-Dihydro-4,9-dimethoxy-7-methyl-7-[(methylthio)methyl]-5H-furo[3,2-g][1]benzopyran-5-one, oxide and 6,7-Dihydro-4,9-dimethoxy-7-methyl-7-[(methylthio)methyl]-5H-furo[3,2-g][1]benzopyran-5-one, dioxide (Formula I: $R_1$ is methyl, $R_2$ is methylsulfinylmethyl or methylsulfonylmethyl, respectively, and $R_3$ and $R_4$ are both methoxy).

Refer to Chart A.

Following the procedure of Example 8, the product of Example 7 is converted to a corresponding sulfoxide or sulfone.

EXAMPLE 11

4,9-Dimethoxy-1′-methoxy-1′-methyl-spiro[7H-furo[3,2-g][1]benzopyran-7,4′-piperidine]-5(6H)-one (Formula I, $R_1$ and $R_2$ taken together are —$(CH_2)_2$—N(CH$_3$)—$(CH_2)_2$—, and $R_3$ and $R_4$ are both methoxy).

Refer to Chart A.

Following the procedure of Example 1 or Example 2, 1-(6-hydroxy-4,7-dimethoxy-5-benzofuranyl)-ethanone (7.35 g) and N-methyl-4-piperidone (6 ml) are transformed to 6.72 g of title product as a tan crystal, melting point 102°–103.1° C. Silica gel TLC $R_f$ is 0.21 in 10% methanol in trichloromethane. IR absorptions (cm$^{-1}$) are observed at 3100, 3060, 2800, 2780, 2760, 1685, 1760, 1625, 1610, 1590, 1545, 1540, 1480, 1150, 1130, and 1075. NMR absorptions (CDCl$_3$, δ) are observed at 7.51, 6.94, 4.10, 4.07, 2.72, 2.7–2.43, 2.35, and 2.2–1.6.

In accordance with the procedures of the examples given above, there are prepared each of the various novel Formula I compounds disclosed herein.

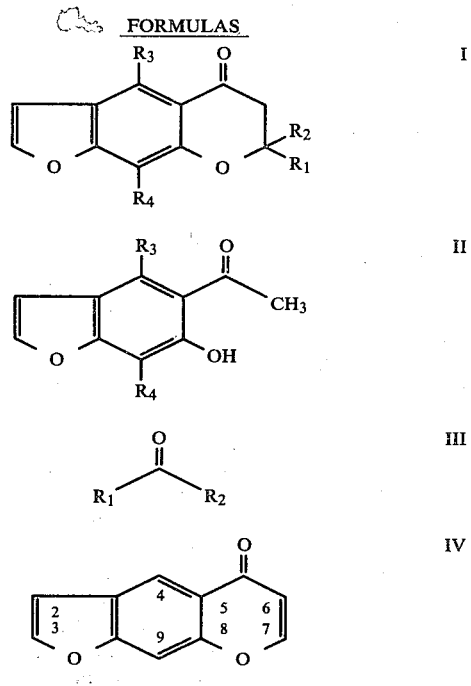

-continued
FORMULAS

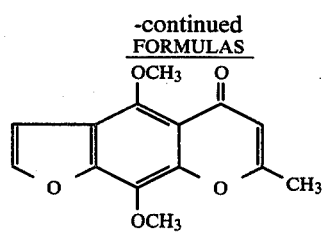
V

CHART A

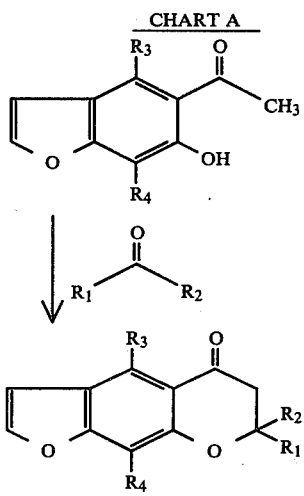

XXI

XXII

XXIII

APPENDIX A

BACKGROUND OF THE INVENTION

The present invention provides novel compositions of matter and processes for their preparation. Particularly, the present invention relates to novel chemical intermediates and associated processes for the preparation of furochromones. Most especially, the present invention provides for the preparation of novel antiatherosclerotic furochromones, particularly khellin analogs.

Khellin and related compounds are known to exert a wide variety of pharmacological effects. Recently, khellin has been reported to exhibit useful antiatherosclerotic activities. Moreover, numerous analogs of khellin likewise are known to exert useful antiatherosclerotic effects. For example, 7-methylthiomethyl-4,9-dimethoxyfurochromone is described in U.S. Pat. No. 4,284,569 as such a useful antiatherosclerotic substance.

Methods for the total synthesis of khellin are known. For example, pyrogallol has been employed as a starting material for the synthesis of furochromones such as khellin. See Clarke, J. R., et al., J. Chem. Soc., 302 (1949), Baxter, R. A., et al., J. Chem. Soc., S30 (1949), Schonberg, A., et al., J. Am. Chem. Soc., 73:2960 (1951), Murti, V. V. S., et al., Proc. of the Indian Acad. of Sci., 30A:107 (1949), and Geissman, T. A., et al., J. Am. Chem. Soc., 73:1280 (1951). Also descriptive of the synthesis of khellin are Spath, E., et al., Chem. Ber., 71:106 (1938), Dann, O., et al., Chem. Ber., 93:2829 (1960), Dann, O., et al., Ann. Chem., 605:146 (1957), and Murti, V. V. S., et al., J. Sci. Ind. Res. (India), 8B:112 (1949). See also U.S. Pat. No. 2,680,119 describing the synthesis of khellin and related compounds.

Other references describing the synthesis of intermediates useful in the preparation of khellin for analogs include: Aneja, R., et al., Chem. Ber., 93:297 (1960),
Aneja, R., et al., J. Sci. Ind. Res. (India), 17B:382 (1958), Gardner, T. S., et al., J. Org. Chem., 15:841 (1950), and Rowe, L. R., et al., Indian J. Chem., 5:105 (1967).

Accordingly, the references cited above describe the preparation of 1-(6-hydroxy-4,7-dimethoxy-5-benzofuranyl)-ethanone. Also known is the related compound 6-hydroxy-4,7-dimethoxy-5-benzofurancarboxylic acid, methyl ester, described by Musante, C., Gazz. Chim. Ital.,

PRIOR ART

Methods of the total synthesis of khellin are known, as are certain chemical intermediates useful in its synthesis.

Most typically, however, the total synthesis of furochromones from benzofurans has been accomplished by utilizing a substituted benzene ring from which to synthesize the fused benzofuran ring system. C. Mustafa, "Benzofurans," John Wiley and Sons, 1974, and Mustafa, A., "Furopyrans and Furopyrones, Chapter 3: Furochromones," John Wiley and Sons, New York, New York, 1967.

U.S. Pat. No. 4,284,569 provides a variety of novel antiatherosclerotic furochromones.

SUMMARY OF THE INVENTION

The present invention particularly provides:
(a) A process for preparing a compound of formula XI which comprises:
(1) reacting the lithium dianion of a compound of formula X with succinic anhydride;
(2) $C_1$–$C_4$ alkyl esterifying the resulting formula XII ketodiacid of step (1);
(3) reacting the resulting formula XIII ketodiester of step (2), wherein $R_{11}$ is $C_1$–$C_4$ alkyl, with an amide acetal of formula XIV, wherein $R_3$ and $R_4$, being the same or different, are $C_1$–$C_4$ alkyl;
(4) cyclizing of the resulting formula XV compound of step (3), wherein $R_3$, $R_4$ and $R_{11}$, are as defined above;
(5) dialkylating the resulting formula XVI benzofuran of step (4), wherein $R_{11}$ is as defined above;
(6) oxidizing the resulting formula XVII dialkoxybenzofuran of step (5), wherein $R_1$ is $C_1$–$C_4$ alkyl and $R_{11}$ is as defined above; and
(7) reducing the resulting formula XVIII compound of step (6), wherein $R_2$ and $R_{11}$ are as defined above, to the formula XI compound;
(b) A furochromone intermediate of formula I or II, wherein $R_{11}$ is $C_1$–$C_4$ alkyl; wherein $R_2$ is hydrogen or $C_1$–$C_4$ alkyl; and wherein $R_{11}$ is as defined above; wherein W is $\alpha$—H:$\beta$—H or =CH—NR$_3$R$_4$; wherein $R_3$ and $R_4$, being the same or different, are as defined above;
(c) A furochromone intermediate of formula III;
(d) A furochromone intermediate of formula IV, wherein $R_{11}$ is as defined above;
(e) A furochromone intermediate of formula V, wherein $R_3$, $R_4$ and $R_{11}$ are as defined as above;
(f) A furochromone intermediate of formula VI, wherein $R_{11}$ is as defined above;
(g) A furochromone intermediate of formula VII, wherein $R_{11}$ is as defined above;
(h) A furochromone intermediate of formula I or II, wherein $R_1$, $R_3$, $R_4$, and $R_{11}$ are all methyl; and
(i) An anti-atherosclerotic furochromone of formula VIII wherein $R_{10}$ is $C_2$–$C_4$ alkyl;
wherein $R_{12}$ is:
  (1) hydrogen;
  (2) $C_1$–$C_8$ alkyl;
  (3) $C_2$–$C_8$ alkoxymethyl;
  (4) $C_2$–$C_8$ alkylthioalkyl;
  (5) trifluoromethyl;
  (6) phenoxymethyl optionally substituted by chloro, fluoro, trifluoromethyl, $C_1$–$C_3$ alkyl or $C_1$–$C_3$ alkoxy;
  (7) phenylthiomethyl optionally substituted by chloro, fluoro, trifluoromethyl, $C_1$–$C_3$ alkyl or $C_1$–$C_3$ alkoxy;
  (8) —$CH_{21}$—$S(O)_n$—$R_{20}$, wherein n is zero, one, or 2 and $R_{20}$ is $C_1$–$C_5$ alkyl; or
  (9) —$CH_2NR_8R_9$, wherein $R_8$ and $R_9$ are hydrogen, $C_1$–$C_{12}$ alkyl or wherein $R_8$ and $R_9$, taken together with N, form a saturated or unsaturated heterocyclic amine ring consisting of from 2 to 7 carbon atoms, inclusive, and zero, one, or 2 additional hetero atoms, with the proviso that said heterocyclic amine ring contains 4 to 8 atoms in the ring, said additional hetero atoms being selected from the group consisting of oxygen, nitrogen, and sulfur, said heterocyclic amine ring being optionally substituted by $C_1$–$C_4$ alkyl, $C_2$–$C_8$ alkylthiomethyl or alkoxymethyl $C_1$–$C_4$ hydroxyalkyl, or phenyl;
wherein $R_{13}$ is:
  (1) hydrogen;
  (2) chloro, iodo, or bromo; or
  (3) —$CH_2$—$S(O)_n$—$R_{20}$ wherein n and $R_{20}$ are as defined above, with the proviso that $R_{13}$ is —$CH_2$—$S(O)_n$—$R_{20}$ only when $R_{14}$ is methyl.

In accordance with the method described above, there is prepared the formula XI benzofuran when $R_1$ is methoxy. This formula XI benzofuran is known to be useful in the preparation of a wide variety of antiatherosclerotic substances, including khellin and various analogs thereof. See U.S. Pat. No. 4,284,569. Similarly there are prepared the novel formula XI benzofurans when $R_1$ is $C_2$–$C_4$ alkoxy. These intermediates are useful in the preparation of novel antiatherosclerotic 4,9-di-($C_2$–$C_4$)-alkoxy-furochromones of formula VIII by means described in U.S. Pat. No. 4,284,569 for the preparation of the corresponding 4,9-dimethoxyfurochromones therein. Moreover, the manner of use of the novel 4,9-di-($C_2$–$C_4$)-alkoxy-furochromones of formula VIII in the treatment and prevention of atherosclerosis is the same as that described in U.S. Pat. No. 4,284,569 for the corresponding 4,9-dimethoxy compounds. Accordingly, the manner of the preparation and pharmacological use of these novel formula VIII compounds is incorporated herein by and reference from the description of the preparation and use in U.S. Pat. No. 4,284,569 of the anti-atherosclerotic 4,9-dimethoxyfurochromones. Among the novel formula VIII compounds herein, the 4,9-diethoxyfurochromones are preferred.

The process of the present invention is more completely understood by reference to the charts below. In these charts, $R_1$, $R_3$, $R_4$, $R_{11}$ $R_{12}$, and $R_{13}$ are as defined above. $R_5$ is:
  (a) hydrogen;
  (b) $C_1$–$C_8$ alkyl;
  (c) $C_2$–$C_8$ alkoxymethyl;
  (d) $C_2$–$C_8$ alkylthioalkyl;
  (e) trifluromethyl;
  (f) phenoxymethyl;
  (g) phenylthiomethyl;
  (h) phenoxymethyl or phenylthiomethyl, either of which is optionally substituted by one chloro, fluoro, trifluoromethyl, $C_1$–$C_3$-alkyl or $C_1$—$C_3$-alkoxy; or
  (i) $C_3$–$C_{10}$ cycloalkyl.

With regard to the substituent W in formula I, this moiety is defined as either =CH—$NR_3R_4$ or $\alpha$—H:-$\beta$—H. In the latter case reflects the fact that each of the valances of the moiety W is a hydrogen atom, one of which is attached in the $\alpha$ configuration with respect to the ring and the other which is attached in the $\beta$ configuration with respect to the ring.

The carbon atom content of various hydrocarbon containing moieties is indicated by a prefix designating the minimum and maximum number of carbon atoms in the moiety, i.e., the prefix $C_i$-$C_j$ indicates a carbon atom content of the integer "i" to the integer "j" carbon atoms, inclusive. Thus, $C_1$–$C_3$ alkyl refers to alkyl of 1–3 carbon atoms, inclusive, or methyl, ethyl, propyl, and isopropyl.

With respect to the charts, Chart A provides a method whereby the known formula XXI compound, 3-furoic acid is transformed to the highly functionalized benzofuran intermediate of formula XXVI useful in the synthesis of khellin and khellin analogs.

With further respect to chart A, the formula XXII compound is prepared from the formula XXI compound by first preparing the dianion of the formula XXII compound. See Knight, D. W., et al., J. Chem. Soc. Perkins, 1125 (1981), and references cited therein. Accordingly, this dianion is generated by treatment of the formula XXII compound with two equivalents of lithium diisopropylamide at low temperature, e.g., −78° C. At this temperature the resulting dianion is stable for several hours.

The dianion is then transformed to the formula XXII compound by treatment with succinic anhydride.

The resulting formula XXII is then esterified to the formula XXIII compound by conventional means. For example, an etherial diazoalkane is employed or, for larger scale synthesis, an alkanol in hydrochloric acid is useful.

The formula XXIII compound is then converted to the formula XXIV compound by reaction at elevated temperature with an N,N-dialkylformamide dimethylacetal. Preferably, N,N-dimethylformamide dimethylacetal is employed at temperatures in excess of 80° C. For example, reaction at 100° C. for 2 hr yields the formula XXIV compound.

Although this reaction preceeds in relatively high yield at elevated temperature, a less complex mixture of products is obtained by reacting the formula XXIII with the desired formamide for prolonged periods, i.e., up to a week. The optimal conditions for the preparation of the formula XXIV compound by this method are the stirring of the formula XXIII reactant in neat N,N-dimethylformamide dimethylacetal employing a trace of p-toluenesulfonic acid. Alternatively base catalysis is employed using alkoxides, e.g., potassium tert-butoxide in an organic solvent.

The formula XXV compound is then prepared from the formula XXIV compound by a Dieckmann cyclization. Preferably the cyclization occurs under basic conditions, e.g., preferably using potassium tert-butoxide in organic solvent, followed by an acid quench. Suitable organic solvents include benzene and tert-butanol, although the preferred solvent is tetrahydrofuran.

Finally, the formula XXVI compound of Chart A is prepared from the formula XXV compound by alkylation. Alkylation can be accomplished quantitatively by treatment of the formula XXV reactant with an alkyliodide in potassium carbonate.

Chart B provides a method whereby the formula XXXI compound, prepared as the formula XXVI compound of Chart A is converted to formula XXXIII intermediate, a compound known to be useful in the preparation of both khellin and analogs thereof. In accordance with the procedure of Chart B, the formula XXXI compound is transformed to the formula XXXII compound by a Baeyer Villager oxidation. For this oxidation, m-chloroperbenzoic acid is employed at ambient temperature in an organic solvent. Tetrahydrofuran or isopropanol represents the preferred solvent for undertaking this oxidation.

Finally, the formula XXXII compound is transformed into the formula XXXIII compound by conversion of the ester group to a methyl ketone. For this purpose a Grignard reagent in the presence of a tertiary amine is employed according to the method of Kikkawa, I., and Yorifuji, T., Synthesis, 887 (1981).

Chart C provides a summary of the method by which the formula XLI compound, prepared as the formula XXXIII compound of Chart B, is transformed to khellin or analogs thereof. The procedures of Chart C are, for example, known in the art from U.S. Pat. No. 4,284,569, wherein Charts A–D of that patent describe the synthesis of the various formula XLII and formula XLIII compounds from the formula XLI starting material.

Accordingly, the charts herein provide a description of the preparation and use of the novel process and compounds of the present invention.

DESCRIPTION OF THE PREFERRED EMBODIMENTS

The present disclosure is more fully understood by the operation of the following examples:

EXAMPLE 1:

3-Carboxy-γ-oxo-2-furanbutanoic acid (Formula XXII).

Refer to Chart A.

Diisopropylamine (202 g) is added to a flame dried 3 neck flask with a mechanical stirrer, dropping funnel and nitrogen inlet. To this amine is added tetrahydrofuran (THF, 600 ml). This solution is then cooled to −78° C. and n-butyllithium (128 g in hexane, 1.6 m) added over 20 min. After complete addition of the n-butyllithium the reaction is stirred for 2.5 h, the last hour of which, the reaction vessel was only 25% submerged in the dry ice bath. At this point, the lithium diisopropylamine (LDH) separates from solution. Two liters of THF are added and a homogeneous solution develops. The reaction is then completely submerged in the dry ice bath and the 3-furoic acid, formula XXI (100 g), in THF (600 ml) is added over 30 minutes. After complete addition of 3-furoic acid the reaction is stirred an additional two hours. At this point, succinic anhydride (100 g) in THF (800 ml) is rapidly added via the addition funnel. A solid almost immediately begins to separate from solution. As the reaction warms to room temperature, quenching is effected with 2 N hydrochloric acid (3 liters). The entire reaction is poured into a portable separatory funnel. The organic layer is separated and the aqueous back extracted with trichloromethane (3 liters). The organic extracts are dried (MgSO$_4$) and solvent removed in vacuo to give an off-white solid which after an ether wash afforded 120 g of pure white title, mp 181°–200° C. IR absorption (cm$^{-1}$) absorptions are observed at 3140, 3120, 2740, 2640, 1740, 1705, 1630, 1615, 1570, 1330, 1270, 1215, 1165, 890 and 775. $^1$H-NMR absorptions (δ, CDCl$_3$) are observed at 7.73, 7.05, 3.38 and 2.71. Mass spectral peaks are observed at 212, 194, 176, 167, 150, 149, 140, 139, 95, 55 and 39.

EXAMPLE 2

3-Carboxy-γ-oxo-2-furanbutanoic acid bis (methyl ester)

(Formula XXIII: R$_{11}$ is methyl).

Refer to Chart A.

The formula XXII product of Example 1 (170 mg) is suspended in trichloromethane (10 ml) and treated with excess diazomethane. When TLC (5% EtOAc/CHCl$_3$) indicated complete conversion to the bismethyl ester, the trichloromethane is removed in vacuo to yield 211 mg of crude product which was chromatographed (Merck B, 5% EtOAc/CHCl$_3$) to yield 211 mg of the pure title product as a colorless oil.

Silica Gel TLC R$_f$ is 0.39 in 5% ethyl acetate in trichloromethane. IR absorptions (cm$^{-1}$) are observed at 3050, 1735, 1695, 1590, 1480, 1440, 1400, 1360, 1305, 1280 and 1160. $^1$H-NMR absorptions (δ, CDCl$_3$) are observed at 7.5, 6.83, 3.90, 3.71, 3.30, and 2.75. Mass spectral peaks are observed at 240, 208, 181, 176, 153, 149, 123, 95, 55 and 38.

EXAMPLE 3

β-[(Dimethylamino)methylene]-3-(methoxycarbonyl)-γ-oxo-2-furanbutanoic acid bis (methylester) (Formula XXIV: R$_3$, R$_4$ and R$_{11}$ are all methyl).

Refer to Chart A.

The formula XXIII product of Example 2 (500 mg) and N,N-dimethylformamide dimethylacetal (230 mg) are heated neat at 100° C. for 1 hour. The reaction is then cooled to room temperature and excess acetal and methanol are removed in vacuo. The resulting brown oil is chromatographed (eluting with 5% methanol in ethyl acetate) to yield 280 mg of title product as a yellow oil.

Silica Gel TLC R$_f$ is 0.4 in 5% methanol in ethyl acetate. IR absorptions (cm$^{-1}$) are observed at 3120, 2950, 1725, 1640, 1560, 1430, 1405, 1390, 1320 and 1160. NMR absorptions (δ, CDCl$_3$) are observed at 7.45, 6.95, 6.73, 3.82, 3.68 and 3.07. Mass spectral peaks are observed at 295, 263, 264, 237, 236, 218, 182, 153, 142 and 139.

EXAMPLE 4

6-Formyl-4,7-dihydroxy-5-benzofurancarboxylic acid methyl ester (Formula XXV: R$_{11}$ is methyl).

Refer to Chart A.

A. (Preparation 1) Potassium metal (50 mg, 1.28 mmol) is added to tert-butanol (5 ml) under nitrogen with stirring. After the potassium metal has dissolved the formula (190 mg), in tert-butanol (5 ml) is added at room temperature. As the drops of diester hit the solution, a deep red color develops. This color slowly fades to yellow with time. After complete addition of the formula XXIV product of Example 3, the reaction is stirred an additional hour and then diluted with water. The reaction acidified with 2 N HCl and was extracted with diethyl ether and then with trichloromethane. The combined organic extracts are dried (MgSO$_4$) and solvent removed in vacuo to yield a brown solid which after chromatography affords 40 mg of title product.

Silica Gel TLC R$_f$ is 0.50 in 5% EtOAc/CHCl$_3$. IR absorptions (cm$^{-1}$) are observed at 3500, 2600, 1670, 1640, 1580, 1430, 1360, 1300, 1250. NMR absorptions ($\delta$, CDCl$_3$) are observed at 10.5, 7.81, 7.0 and 4.0. Mass spectral peaks are observed at 236, 205, 204, 203, 176, 149, 148, 147, 119 and 63.

B. (Preparation 2) Potassium tert-butoxide (319 mg) is added to 20 ml of dry THF under nitrogen. This mixture is then cooled to $-78°$ C. and the formula XXIV starting material (420 mg) in THF (15 ml) added via syringe pump at a rate of 0.23 ml/min. A deep red color developes. After complete addition the reaction is stirred an additional 30 minutes and then the reaction is quenched at $-78°$ C. by the addition of 2 N HCl. The reaction is then warmed to room temperature and poured into a separatory funnel. Then 2 N HCl (50 ml) is added and the reaction was extracted with ethyl acetate (3×75 ml). The aqueous layer is then extracted with trichloromethane. The combined organic extracts are dried (MgSO$_4$) and solvent removed in vacuo to 340 mg of a brown solid. This solid is chromatographed over silica gel eluting with 5% ethyl acetate in trichloromethane to yield 200 mg of title product.

EXAMPLE 5

6-Formyl-4,7-dimethoxy-5-benzofurancarboxylic acid methyl ester (Formula XXVI: R$_1$ and R$_{11}$ are methyl).

Refer to Chart A.

6-Formyl-4,7-dihydroxy-5-benzofurancarboxylic acid methyl ester (Example 4, 4.70 g) is added to acetone (100 ml) followed by addition of methyliodide (5.65 g) and potassium carbonate (5.0 g). The resulting mixture is heated at reflux for 24 hr. The reaction is cooled to room temperature and trichloromethane (100 ml) is added. Water (200 ml) is added. The organic layer is separated and the aqueous layer back extracted with trichloromethane (2×75 ml). The combined organic layer is dried (MgSO$_4$) and solvent removed in vacuo to yield a yellow oil. Chromatography over 100 g of silica gel eluting with 5% ethyl acetate in trichloromethane affords 5.2 g of title product as a pale yellow oil that slowly crystallized on standing. A pure product is prepared by recrystallization from methanol, mp 89.9°–90.8° C.

Silica Gel TLC R$_f$ is 0.44 in 5% EtOAc/CHCl$_3$. IR absorptions (cm$^{-1}$) are observed at 1730, 1680, 1600, 1470, 1440, 1390, 1340, 1305, 1290, 1060, 980 and 930. NMR absorptions ($\delta$, CDCl$_3$) are observed at 10.4, 7.83, 6.97, 4.38 and 3.98. Mass spectral peaks are observed at 264, 249, 236, 233, 221, 205, 203, 189 and 147.

EXAMPLE 6

6-Hydroxy-4,7-dimethoxy-5-benzofurancarboxylic acid, methyl ester (Formula XXXII: R$_1$ and R$_{11}$ are methyl).

Refer to Chart B.

A. (Procedure I) A solution of 6-Formyl-4,7-dimethoxy-5-benzofurancarboxylic acid, methyl ester (Example 5, 104.0 mg) in isopropanol (8.0 ml) is treated with 85% m-chloroperbenzoic acid (MCPBA, 188 mg) at ambient temperature and stirred overnight. The solvent is removed on the rotary evaporator and the residue is taken up into 10% aqueous sodium carbonate (10 ml) and diethyl ether (10 ml). After stirring for 30 minutes the layers are separated and the aqueous is extracted with additional diethyl ether (1×20 ml). The ether extracts are combined and dried (MgSO$_4$). The residue is chromatographed (20 g silica gel) eluting with 20% ethyl acetate in isomeric hexanes (Skellysolve B) to provide 63.2 mg of white solid, title product, mp 82°–84° (yield 63%).

B. (Procedure II) When the reaction is repeated as above substituting THF as the solvent, 101.5 mg of starting material and 184 mg of MCPBA yields 30.0 mg of pure product, mp 82°–84°.

EXAMPLE 7

1-(6-Hydroxy-4,7-dimethoxy-5-benzofuranyl)-ethanone (Formula XXXIII: R$_1$ is methyl).

A. A 100 ml 3 neck flask is oven dried and cooled under nitrogen. Benzene (10 ml) is placed in the flask followed by methyl magnesium bromide (2.9 M in diethyl ether, 2.0 ml). To that solution is added dry triethylamine (2.45 ml) and the resulting mixture is cooled to 8°–10°. A solution of 6-hydroxy-4,7-dimethoxy-5-benzofurancarboxylic acid methyl ester (Example 6, 250 g) in dry benzene (15 ml) is then added dropwise to the cold reaction mixture over a 15 min period. The resulting mixture is yellow; the ice bath is removed and stirring continued at ambient temperature for 6.5 hours.

B. The reaction mixture is then cooled in ice and quenched by the addition of saturated ammonium chloride (10 ml). Diethyl ether (40 ml) is next added, along with 2 N HCl (30 ml). The layers are separated, the ether layer dried (MgSO$_4$) and concentrated to an oil. This crude mixture was heated with 10 ml of 5% aqueous potassium hydroxide for 2 hr. The mixture is then carefully acidified (6 N HCl) and extracted with ethyl acetate (3×25 ml). The combined organic extracts are washed with saturated sodium bicarbonate (2×20 ml) and dried (MgSO$_4$). Evaporation of the solvent yields 0.13 g of yellow solid which is chromatographed (on silica gel eluting with 20% ethyl acetate in Skellysolve B SSB eluent) to afford 0.128 g of title product. Recrystallization of that material (hexane/ethyl acetate, 10:1) yields 85 mg of pure, bright yellow title product as a solid.

The product of Example 7 is identical to the product of Example 1 of U.S. Pat. No. 4,284,569 and is accordingly useful for the preparation of khellin and analogs thereof, e.g., see Examples 2–21 of U.S. Pat. No. 4,284,569.

EXAMPLE 8

7-methylthiomethyl-4,9-diethoxyfurochromone (Formula XLIII: R$_1$ is ethyl, R$_{12}$ is methylthiomethyl, and R$_{13}$ is methyl).

Refer to Chart C.

A. 6-Formyl-4,7-dihydroxy-5-benzofurancarboxylic acid methyl ester (Example 4, 4.70 g) is added to acetone (100 ml) followed by addition of ethyliodide (5.80 g) and potassium carbonate (5.0 g). The resulting mixture is heated at reflux for 24 hr. The reaction is cooled to room temperature and trichloromethane (100 ml) is added. Water (200 ml) is added. The organic layer is separated and the aqueous layer back extracted with trichloromethane (2×75 ml). The combined organic layer is dried (MgSO$_4$) and solvent removed in vacuo to yield a reaction. Chromatography over 100 g silica gel eluting with 5% ethyl acetate in trichloromethane affords product.

B. A solution of 6-Formyl-4,7-diethoxy-5-benzofurancarboxylic acid, methyl ester (part A, 105.0 mg) in isopropanol (8.0 ml) is treated with 85% m-chloroperbenzoic acid (m-CPBA, 188 mg) at ambient temperature and stirred overnight. The solvent is removed on the rotary evaporator and the residue is taken up into 10% aqueous sodium carbonate (10 ml) and diethyl ether (10 ml). After stirring for 30 minutes the layers are separated and the aqueous is extracted with additional diethyl ether (1×20 ml). The ether extracts are combined and dried (MgSO$_4$). The residue is chromatographed (20 g silica gel) eluting with 20% ethyl acetate in isomeric hexanes (Skellysolve B) to provide product.

C. A 100 ml 3 neck flask is oven dried and cooled under nitrogen. Benzene (10 ml) is placed in the flask followed by methyl magnesium bromide (2.9 M in diethyl ether, 2.0 ml). To that solution is added dry triethylamine (2.45 ml) and the resulting mixture is cooled to 8°–10°. A solution of 6-hydroxy-4,7-dimethoxy-5-benzofurancarboxylic acid methyl ester (part B, 250 g) in dry benzene (15 ml) is then added dropwise to the cold reaction mixture over a 15 min period. The ice bath is removed and stirring continued at ambient temperature for 6.5 hours.

D. The reaction mixture of part C is then cooled in ice and quenched by the addition of saturated ammonium chloride (10 ml). Diethyl ether (40 ml) is next added, along with 2 N HCl (30 ml). The layers are separated, the ether layer dried (MgSO$_4$) and concentrated to an oil. This crude mixture was heated with 10 ml of 5% aqueous potassium hydroxide for 2 hr. The mixture is then carefully acidified (6 N HCl) and extracted with ethyl acetate (3×25 ml). The combined organic extracts are washed with saturated sodium bicarbonate (2×20 ml) and dried (MgSO$_4$). Evaporation of the solvent yields a residue which is chromatographed (on silica gel eluting with 20% ethyl acetate in Skellysolve B eluent) to afford product.

E. To sodium hydride (20.1 g of a 50% dispersion in oil) and tetrahydrofuran (20 ml freshly distilled from lithium aluminum hydride), combined under a nitrogen atmosphere to form a slurry, are added dropwise a mixture of the product of part D (56 g), ethyl 2-(methylthio)-acetate (26.4 g) and dry tetrahydrofuran (50 ml). After the addition is complete (1.5 hr) the reaction mixture is then heated on a steam bath for 15 min and cooled to ambient temperature. Thereupon excess sodium hydride is destroyed by careful addition of ice and water (300 ml). Washing with diethyl ether (600 ml) yields an aqueous layer which is diluted with methanol (100 ml) and concentrated hydrochloric acid (75 ml). This mixture is then refluxed for 45 min and thereupon allowed to cool at ambient temperature. Upon extraction with methylene chloride (600 ml) the organic extracts are dried and concentrated under reduced pressure to yield pure title product.

FORMULAS

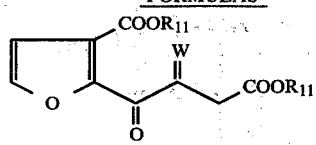

I

-continued
FORMULAS

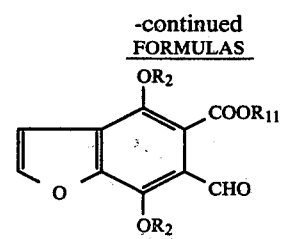

II

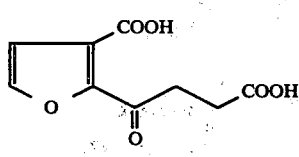

III

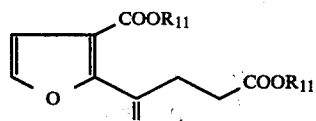

IV

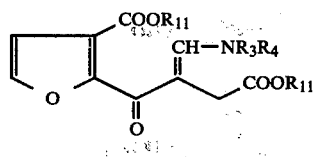

V

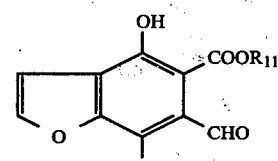

VI

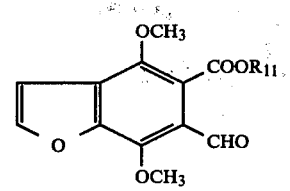

VII

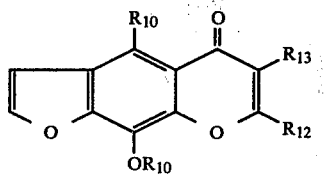

VIII

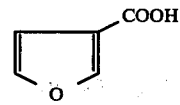

X

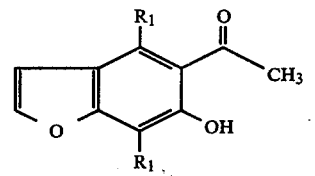

XI

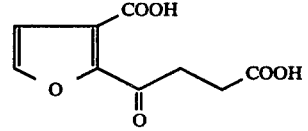

XII

-continued
FORMULAS
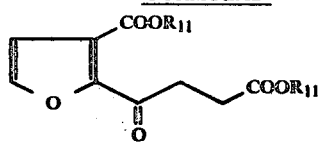 XIII
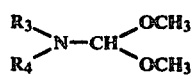 XIV
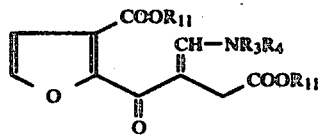 XV
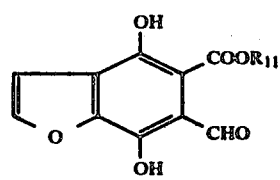 XVI
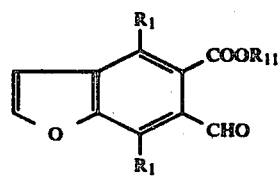 XVII
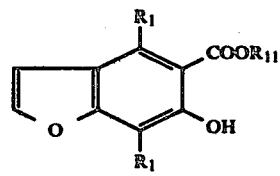 XVIII
CHART A
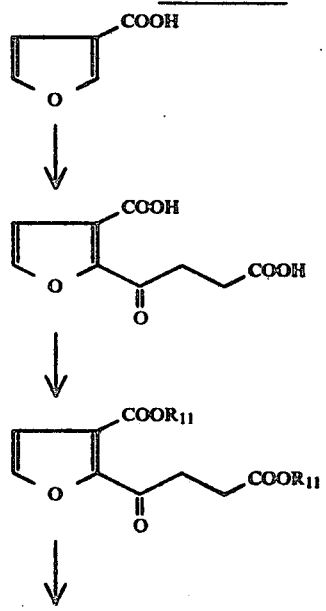
XXI
XXII
XXIII
-continued
CHART A
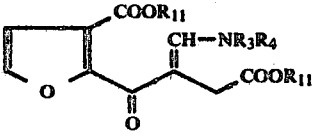 XXIV
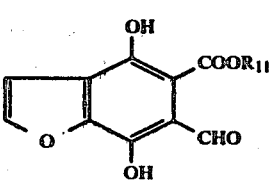 XXV
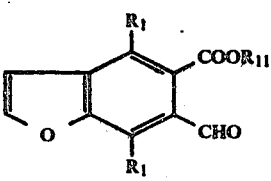 XXVI
CHART B
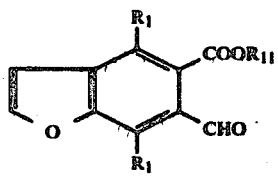 XXXI
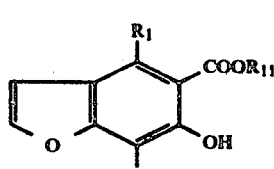 XXXII
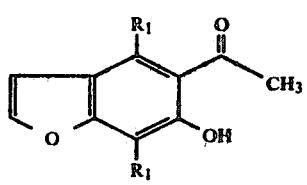 XXXIII

CHART C

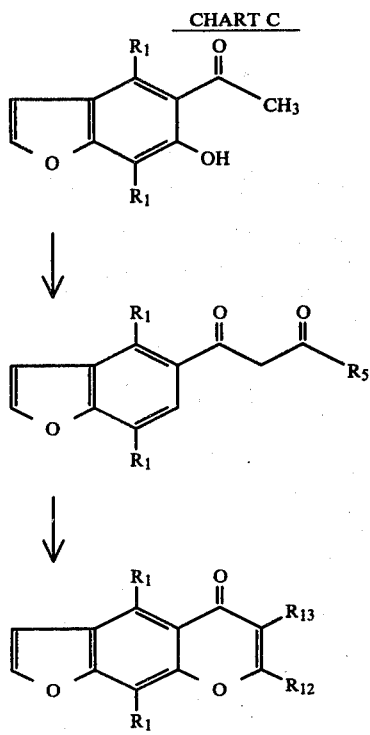

APPENDIX B

BACKGROUND OF THE INVENTION

The present invention provides novel compositions of matter and processes for their preparation. Particularly, the present invention relates to novel chemical intermediates and associated processes for the preparation of furochromones. Most especially, the present invention provides for the preparation of novel antiatherosclerotic furochromones, particularly khellin analogs.

Khellin and related compounds are known to exert a wide variety of pharmacological effects. Recently, khellin has been reported to exhibit useful antiatherosclerotic activities. Moreover, numerous analogs of khellin likewise are known to exert useful antiatherosclerotic effects. For example, 7-methylthiomethyl-4,9-dimetoxyfurochromone is described in U.S. Pat. No. 4,284,569 as such a useful antiatherosclerotic substance.

Methods for the total synthesis of khellin are known. For example, pyrogallol has been employed as a starting material for the synthesis of furochromones such as khellin. See Clarke, J. R., et al., J. Chem. Soc., 302 (1949), Baxter, R. A., et al., J. Chem. Soc., S30 (1949), Schonberg, A., et al., J. Am. Chem. Soc., 73:2960 (1951), Murti, V. V. S., et al., Proc. of the Indian Acad. of Sci., 30A:107 (1949), and Geissman, T. A., et al., J. Am. Chem. Soc., 73:1280 (1951). Also descriptive of the synthesis of khellin are Stath, E., et al., Chem. Ber., 71:106 (1938), Dann, O., et al., Chem. Ber., 93:2829 (1960), Dann, O., et al., Ann. Chem., 605:146 (1957), and Murti, V. V. S., et al., J. Sci. Ind. Res. (India), 8B:112 (1949). See also U.S. Pat. No. 2,680,119 describing the synthesis of khellin and related compounds.

Other references describing the synthesis of intermediates useful in the preparation of khellin for analogs include: Aneja, R., et al., Chem. Ber., 93:297 (1960), Aneja, R., et al., J. Sci. Ind. Res. (India), 17B:382 (1958), Gardner, T. S., et al., J. Org. Chem., 15:841 (1950), and Rowe, L. R., et al., Indian J. Chem., 5:105 (1967).

Accordingly, the references cited above describe the preparation of 1-(6-hydroxy-4,7-dimethoxy-5-benzofuranyl)-ethanone. Also known is the related compound 6-hydroxy-4,7-dimethoxy-5-benzofurancarboxylic acid, methyl ester, described by Musante, C., Gazz. Chim. Ital., 88:910 (1958).

PRIOR ART

Methods of the total synthesis of khellin are known, as are certain chemical intermediates useful in its synthesis.

The use of pyrogallol in the synthesis of khellin intermediates is known. For example, the transformation of pyrogallol to the khellin intermediate 1-(2,3-dihydro-6,7-dihydroxy-5-benzofuranyl) ethanone is known. The parahydroxylation of this intermediate is also known. See Row, L. R., et al., Indian J. Chem., 5:105 (1967) describing this transformation and the subsequent dimethylation to yield known khellin intermediates. U.S. Pat. No. 4,284,569 provides a variety of novel anti-atherosclerotic furochromones.

SUMMARY OF THE INVENTION

The present invention particularly provides:
(a) A method of preparing a dialkoxybenzofuran of formula I,
wherein $R_2$ and $R_3$ are $C_1$-$C_4$ alkyl, being the same or different, which comprises para-alkoxylating a monoalkoxybenzofuran of formula II, wherein $R_2$ is as defined above, with an oxidizing reagent selected from the group consisting of
  (i) thallium (III) nitrate, (ii) ceric ammonium nitrate,
  (iii) lead tetraacetate, in a $C_1$-$C_4$ alkanol solvent of formula $R_3OH$,
wherein $R_3$ is as defined above;
(b) A benzofuran of formula III,
wherein $R_2$ is $C_1$-$C_4$ alkyl;
(c) A benzofuran of formula IV,
wherein $R_5$ is $C_2$-$C_4$ alkyl;
(d) A benzofuran of formula V,
wherein one of $R_6$ and $R_7$ is $C_1$-$C_4$ alkyl and the other is $C_2$-$C_4$ alkyl with the proviso that $R_6$ and $R_7$ are different;
(e) An anti-atherosclerotic furochromone of formula VI,
wherein $R_6$ and $R_7$ are as defined above;
wherein $R_{12}$ is:
  (1) hydrogen;
  (2) $C_1$-$C_8$ alkyl;
  (3) $C_2$-$C_8$ alkoxymethyl;
  (4) $C_2$-$C_8$ alkylthioalkyl;
  (5) trifluoromethyl;
  (6) phenoxymethyl optionally substituted by chloro, fluoro, trifluoromethyl, $C_1$-$C_3$ alkyl or $C_1$-$C_3$ alkoxy;
  (7) phenylthiomethyl optionally substituted by chloro, fluoro, trifluoromethyl, $C_1$-$C_3$ alkyl or $C_1$-$C_3$ alkoxy;
  (8) —$CH_{21}$—$S(O)_n$—$R_{20}$, wherein n is zero, one or 2 and $R_{20}$ is $C_1$-$C_5$ alkyl; or
  (9) —$CH_2NR_8R_9$, wherein $R_8$ and $R_9$ are hydrogen, $C_1$-$C_{12}$ alkyl or wherein $R_8$ and $R_9$, taken together with N, form a saturated or unsaturated heterocyclic amine ring consisting of from 2 to 7 carbon atoms, inclusive, and zero, one, or 2 additional hetero atoms, with the proviso that said heterocyclic amine ring contains 4 to 8 atoms in the ring, said additional hetero atoms being selected from the group consisting of oxygen, nitrogen, and sulfur, said heterocyclic amine ring being optionally substituted by $C_1$–$C_4$ alkyl, $C_2$–$C_8$ alkylthiomethyl or alkoxymethyl $C_1$–$C_4$ hydroxyalkyl, or phenyl;

wherein $R_{13}$ is:
(1) hydrogen;
(2) chloro, iodo, or bromo; or
(3) —$CH_2$—$S(O)_n$—$R_{20}$ wherein n and $R_{20}$ are as defined above, with the proviso that $R_{13}$ is —$CH_2$—$S(O)_n$—$R_{20}$ only when $R_{14}$ is methyl;

(f) 4-Ethoxy-9-methoxy-7-methylthiomethylfurochromone; and
(g) 4-Methoxy-9-ethoxy-7-methylthiomethylfurochromone.

In accordance with the method described above, there is prepared the formula II alkoxybenzofuran. This formula II alkoxybenzofuran wherein $R_2$ is methyl is known to be useful in the preparation of a wide variety of anti-atherosclerotic substances, including khellin and various analogs thereof. See U.S. Pat. No. 4,284,569.

Similarly there are prepared the novel formula XI benzofurans when $R_1$ is $C_2$–$C_4$ alkoxy. These intermediates are useful in the preparation of novel anti-atherosclerotic 4,9-di-($C_2$–$C_4$)-alkoxy-furochromones of formula VIII by means described in U.S. Pat. No. 4,284,569 for the preparation of the corresponding 4,9-dimethoxyfurochromones therein. Moreover, the manner of use of the novel 4,9-di-($C_2$–$C_4$)-alkoxy-furochromones of formula VIII in the treatment and prevention of atherosclerosis is the same as that described in U.S. Pat. No. 4,284,569 for the corresponding 4,9-dimethoxy compounds. Accordingly, the manner of the preparation and pharmacological use of these novel formula VIII compounds is incorporated herein by and reference from the description of the preparation and use in U.S. Pat. No. 4,284,569 of the antiatherosclerotic 4,9-dimetoxyfurochromones. Among the novel formula VIII compounds herein, the 4,9-diethoxyfurochromones are preferred.

The process of the present invention is more completely understood by reference to the charts below. In these charts, $R_1$ is hydrogen or $C_1$–$C_4$ alkyloxy or hydrogen. $R_2$, $R_3$, $R_{12}$ and $R_{13}$ are as defined above.

$R_{11}$ is:
(a) hydrogen;
(b) $C_1$–$C_8$ alkyl;
(c) $C_2$–$C_8$ alkoxymethyl;
(d) $C_2$–$C_8$ alkylthioalkyl;
(e) trifluromethyl;
(f) phenoxymethyl;
(g) phenylthiomethyl;
(h) phenoxymethyl or phenylthiomethyl, either of which is optionally substituted by one chloro, fluoro, trifluoromethyl, $C_1$–$C_3$-alkyl, or $C_1$–$C_3$- alkoxy; or
(i) $C_3$–$C_{10}$ cycloalkyl.

The carbon atom content of various hydrocarbon containing moities is indicated by a prefix designating the minimum and maximum number of carbon atoms in the moiety, i.e., the prefix $C_i$–$C_j$ indicates a carbon atom content of the integer "i" to the integer "j" carbon atoms, inclusive. Thus, $C_1$–$C_3$ alkyl refers to alkyl of 1–3 carbon atoms, inclusive, or methyl, ethyl, propyl, and isopropyl.

With respect to the charts, Chart A provides a method whereby the known formula XXI compound is transformed to the novel formula XXV 2,3-dihydrobenzofuran, which is in turn reduced to the known formula XXVI benzofuran intermediate for preparing desmethoxy khellin and other khellin analogs.

With further respect to Chart A, pyrogallol is converted to the formula XXII triacetate first by treatment with chloroacetonitrile according to procedures described by Geissman, T. A., et al., J. Amer. Chem. Soc., 73:57–65 (1951).

Thereafter the formula XXIII production product is obtained from the formula XXII compound employing a metal catalyst under a hydrogen atmosphere. For example, conventional metal catalysts such as palladium and carbon catalysts are employed. See Dann, O. and Zeller, H. G., Ber. 93:28–29 (1960) for a transcription of this transformation.

Thereafter the formula XXIII compound then to go to Fries rearrangement to yield formula XXIV dihydroxy ketone. By this procedure, the formula XXIII compound is treated with a mixture of aluminium trichloride and nitrobenzene.

This formula XXIV compound is then selectively $C_1$–$C_4$ alkylated to the formula XXV compound by treatment with an alkyl iodide. Any concomitant desalkoxylation in this reaction is reversed by treatment with hydrobromic acid.

This novel formula XXV compound is then dehydrogenated using 2,3-dichloro-5,6-dicyanobenzoquinone (DDQ). See Linn, Y. Y., et al., J. Heterocyclic Chem., 799 (1979).

The formula XXVI compound thusly prepared is a highly useful intermediate in the synthesis of analogs of khellin, specifically the 4-desmethoxy khellin. See, for example, U.S. Pat. No. 4,284,569, describing the synthesis of such analogs from the formula XXVI compound wherein $R_2$ is methyl.

With respect to Chart C, a method is provided for the paraalkoxylation of the formula XXXI compound, prepared as the formula XXVI compound in Chart A. This methoxylation preceeds by the use of an oxidizing agent in a $C_1$–$C_4$ alkanol solvent corresponding to the alkoxy group to be introduced at $C_4$. $Ce(NH_4)_2(ND_3)_6$ or $Pb(OAc)_4$ may be employed as the oxidizing agent. See Brother, A. E., et al., Helv. Chim. Acta., 35:9–10 (1952). Alternatively, however, thallium (III) nitrate is employed as the oxidizing agent. See Taylor, E. C., J. Organic Chem., 41:282 (1976). In the latter case, maximum yields are obtained when the oxidizing agent is added over a period of about 15 min with the reaction mixture being maintained at about −25° C. for 30 min followed by heating for 1–2 min.

Chart C provides an illustration of the method by which the formula XLI compound, prepared as the formula XXVI compound of Chart A or the formula XXXII compound of Chart B, is transformed to khellin 4-desmethoxy khellin or analogs thereof. Procedures of Chart C are, for example, known in the art from U.S. Pat. No. 4,284,569 wherein Chart A of that patent describes the synthesis of the various formula XLII and formula XLIII compounds from the formula XLI starting material. Accordingly, the charts herein provide a description of the preparation and use of the novel process and compounds of the present invention.

DESCRIPTION OF THE PREFERRED EMBODIMENTS

The present disclosure is more fully understood by the operation of the following examples:

EXAMPLE 1

3,6,7-Benzofurantriol triacetate (Formula XXII)

Refer to Chart A.

Dry zinc chloride (38 g) is added to pyrogallol (Formula XXII, 35 g). To these solids under a nitrogen atmosphere is added diethyl ether and chloroacetonitrile (18 ml). The resulting mixture is then stirred and cooled to 0° C. Hydrochloride gas is then bubbled to the reaction mixture for 30 min, the mixture is allowed to warm slowly to ambient temperature with stirring for 12 hr. Thereafter, the two-face mixture is cooled to 0° C. and the ether layer decanted. Additional diethyl ether (100 mg) is added, stirred, and decanted. Water (250 ml) is added to the resulting residue and the aqueous mixture is then refluxed for 30 min yielding a homogeneous solution. The solution is then cooled to 4° C., filtered, and yields a reddish-brown solid (24.5 g), α-chlorogallacetophenone. Without further purification, the solid is then dissolved in ethanol (300 ml) containing sodium acetate (24.5 g). After refluxing for 5 hr, the resulting mixture is then dried and treated with acetic anhydride (150 ml) and pyridine (75 ml). The resulting mixture is then stirred at ambient temperature for 12 hr, decanted into ice water (700 ml) and stirred for one hr. The resulting precipitate is then collected on a filter, washed with water and air dried. Thereafter, the filtrate is acidified with coconcentrated hydrochloric acid and extracted with ethyl acetate. The organic extracts are then washed thoroughly with saturated sodium bicarbonated brine, dried over magnesium sulphate, and concentrated to a residue. Chromatography on 1.3 kg of silica gel alluding with 40% ethyl acetate Skellysolve B ethyl acetate to obtain 27.75 g of pure product, a white solid, melting point 99°–101° C.

EXAMPLE 2

2,3-Dihydro-6,7-benzofurandiol diacetate (Formula XXIII)

A mixture of the title product of Example 1 (50 g) in ethyl acetate (350 ml) is treated with anhydrus potassium acetate (7.5 g) and 7.5 g of a 10% paladium on carbon catalyst. The reaction mixture is then hydrogenated at 65° C. for 2 hr, cooled to ambient temperature, and filtered through diaconaceous earth. The resulting filtrate is then concentrated under reduced pressure yielding a solid. Recrystallization from 250 ml of ethyl acetate and Skellysolve B (1:1) yields 33.65 g of pure title product as a white solid, melting point 114°–115° C. Silica gel TLC $R_f$ is 0.31 in 25% ethyl acetate in hexane. IR absorptions (cm$^{-1}$) are observed at 1765, 1625, 1490, 1610, 1465, 1375, 1225, 1210, 1180, and 1035. NMR absorptions are observed at 7.05, 6.62, 4.64, 3.21, 2.25, and 2.23 δ.

EXAMPLE 3

1-(2,3-dihydro-6,7-dihydroxy-5-benzofuranyl)-ethanone (Formula XXIV)

Refer to Chart A.

A mixture of the title product of Example 2 (9.50 g), nitrobenzene (100 ml) and aluminium trichloride (6.36 g) is heated at 60° C. for 90 min. After cooling to ambient temperature, the reaction mixture is poured over ice and 2 N hydrochloric acid (100 ml) is added, followed by the addition of water (300 ml). After stirring for 3 hr, the reaction mixture is then extracted with ethyl acetate. The organic layer is then separated and washed with 5% aqueous sodium hydroxide and the aqueous layer then poured into 2 N hydrochloric acid (500 ml), yielding a precipitate. Ethyl acetate is then added and then separated from the aqueous layer. The organic layer is then dried over magnesium sulphate and concentrated under reduced pressure to yield 6.35 g of title product as a brown solid. Recrystallization from ethyl acetate yields pure crystalline product, melting point 190°–190.5° C. Silica gel TLC $R_f$ is 0.25 in 5% ethyl acetate in trichloromethane. IR absorptions (cm$^{-1}$) are observed at 3460, 3200, 1645, 1605, 1490, 1445, 1365, 1320, 1255, and 1055. NMR absorptions are observed at 7.15, 4.70, 3.18, and 2.52 δ.

EXAMPLE 4

1-(2,3-dihydro-6-hydroxy-7-methoxy-5-benzofuranyl)ethanone (Formula XXV: $R_2$ is methyl)

Refer to Chart A.

A mixture of the title product of Example 3 (5.9 g) potassium carbonate (12 g) and methyl iodide (25 g) is heated at reflux and acetone for 18 hr. After cooling to ambient temperature and removal of the potassium carbonate by filtration, the resulting mixture is then concentrated under reduced pressure to a yellow oil. The oil is then dissolved in trichloromethane and treated with hydrobromic acid and refluxed for 2 hr. After cooling to ambient temperature and concentration under reduced pressure, chromatography eluting with 5% ethyl acetate in trichloromethane yields 6.0 g of pure title product, melting point 95°–97° C. Silica gel TLC $R_f$ is 0.5 in 5% ethyl acetate in trichloromethane. IR absorptions (CM$^{-1}$) are observed at 2700, 1630, 1615, 1430, 1405, 1365, 1330, 1290, and 1060. NMR absorptions are observed at 7.3, 6.48, 3.9, and 3.15 δ.

EXAMPLE 5

1-(6-hydroxy-7-methoxy-5-benzofuranyl)-ethanone (Formula XXVI: $R_2$ is methyl)

Refer to Chart A.

To a solution of the title product of Example 4 (12.1 g) in dioxane is added 2,3-dichloro-5,6-dicyanobenzoquinone (DDQ, 17.8 g). The resulting black solution is then stirred at reflux for 2 hr. Upon cooling to ambient temperature, a precipitate forms. The reaction mixture is then filtered and the filter cake is washed with dichloromethane. The filtrate is then concentrated to a residue and the residue chromatographed on 700 g of silica gel eluting with dichloromethane. Pure title product is obtained as 5.5 g of an oil which spontaneously crystallizes. Recrystallization from ethyl acetate in hexane (1:5) yields pure title product, melting point 61.2°–63.5° C. Silica gel TLC $R_f$ is 0.31 in 25% ethyl acetate in hexane. IR absorptions (CM$^{-1}$) are observed at 3140, 3110, 2720, 1635, 1625, 1545, 1320, 1300, 1275, and 1050. NMR absorptions are observed at 7.78, 7.65, 4.21, and 2.71 δ.

EXAMPLE 6

1-(6-hydroxy-4,7-dimethoxy-5-benzofuranyl)-ethanone (Formula XXXII: $R_2$ and $R_3$ are both methyl)

Refer to Chart B.

A. The title product of Example 5 (100 mg) is added to methanol (4 ml) and cooled to −25° C. To the resulting heterogeneous mixture is added a methanolic (7 ml) solution of thallium (III) nitrate trihydrate, TL $(ONO_2)_3.3H_2O$ (250 mg), dropwise over about 15 min. The resulting mixture is then stirred for 30 min at −25° C. and heated to reflux for 1-2 min. The reaction is then poured into saturated aqueous sodium bicarbonate and extracted with diethyl ether. The etheral layer is then dried over magnesium sulphate and concentrated under reduced pressure to yield a yellow oil. Crystallization is achieved by dissolving the oil in 1% ethyl acetate in hexane and cooling to 0° C. for 12 hr. Filtration of the resulting crystals yields 70 mg of pure title product, melting point 98°–99° C. Silica gel TLC $R_f$ is 0.6 in ethyl acetate at hexane (1:1). IR absorptions $(CM^{-1})$ are observed at 2955, 2930, 2926, 2868, 1629, 1619, 1587, 1471, 1452, 1444, 1425, 1382, 1364, 1303, 1267, 1151, 1079, 1061, and 755. NMR absorptions are observed at 7.5, 6.9, 4.15, 4.05, and 2.7 $\delta$.

B. Alternatively title product is prepared utilizing lead tetraacetate (200 mg) which is added to methanol (6 ml) and cooled to 0° C. To the resulting solution is added the title product of Exaple 5 (100 mg) dropwise in methanol (5 ml). The resulting mixture is then stirred at 0° C. for 80 min and poured into saturated aqueous sodium bicarbonate. After extraction with ether, the etheral solution is then dried over magnesium sulphate and concentrated under reduced pressure to yield a yellow oil. This crude solid is then dissolved in methanol and heated at reflux for 1 hr. After cooling to ambient temperature and removal of solvent under reduced pressure, crystallization from 1% ethyl acetate in hexane yields 70 mg of pure title product, melting point 98°–100° C.

EXAMPLE 7

7-Methylthiomethiomethyl-7-methoxy-9-ethoxy-furochromone (Formula XXIII: $R_1$ is methyl, $R_2$ is ethyl, $R_{12}$ is methylthiomethyl, and $R_{13}$ is hydrogen)

Refer to Charts A, B, and C.

A. A mixture of the title product of Example 3 (5.9 g) potassium carbonate (12 g) and ethyl iodide (28 g) is heated at reflux and acetone for 18 hr. After cooling to ambient temperature and removal of the potassium carbonate by filtration, the resulting mixture is then concentrated under reduced pressure. The residue is then dissolved in trichloromethane and treated with hydrobromic acid and refluxed for 2 hr. After cooling to ambient temperature and concentration under reduced pressure, chromatography eluting with 5% ethyl acetate in trichloromethane yields 6.0 g of formula XXV product.

B. To a solution of the product of Part A (12 g) in dioxane is added 2,3-dichloro-5,6-dicyanobenzoquinone (DDQ, 17.8 g). The resulting black solution is then stirred at reflux for 2 hr. Upon cooling to ambient temperature, a precipitate forms. The reaction mixture is then filtered and the filter cake is washed with dichloromethane. The filtrate is then concentrated to a residue and the residue chromatographed on 700 g of silica gel eluting with dichloromethane to obtain formula XXVI product, 1-(6-hydroxy-7-ethoxy-5-benzofuranyl)-ethanone.

C. The formula XXVI product of Part B (100 mg) is added to methanol (4 ml) and cooled to −25° C. To the resulting mixture is added a methanolic (7 ml) solution of thallium (III) nitrate trihydrate, TL $(ONO_2)_3.3H_2O$ (250 mg), dropwise over about 15 min. The resulting mixture is then stirred for 30 min at −25° C. and heated to reflux for 1-2 min. The reaction is then poured into saturated aqueous sodium bicarbonate and extracted with diethyl ether. The etheral layer is then dried over magnesium sulphate and concentrated under reduced pressure to yield formula XXXII product, 1-(6-hydroxy-4-methoxy-7-ethoxy-5-benzofuranyl)-ethanone.

D. To sodium hydride (20.1 g of a 50% dispersion in oil) and tetrahydrofuran (20 ml freshly distilled from lithium aluminum hydride), combined under a nitrogen atmosphere to form a slurry, are added dropwise a mixture of the product of Part C (56 g), ethyl 2-(methylthio)-acetate (26.4 g) and dry tetrahydrofuran (50 ml). After the addition is complete (1.5 hr) the reaction mixture is then heated on a steam bath for 15 min and cooled to ambient temperature. Thereupon excess sodium hydride is destroyed by careful addition of ice and water (300 ml). Washing with diethyl ether (600 ml) yields an aqueous layer which is diluted with methanol (100 ml) and concentrated hydrochloric acid (75 ml). This mixture is then refluxed for 45 min and thereupon allowed to cool to ambient temperature. Upon extraction with methylene chloride (600 ml) the organic extracts are dried and concentrated under reduced pressure to yield pure title product.

EXAMPLE 8

7-Methylthiomethiomethyl-4-ethoxy-9-methoxyfurochromone (Formula XXIII: $R_1$ is ethyl, $R_2$ is methyl, $R_{12}$ is methylthiomethyl, and $R_{13}$ is hydrogen.)

Refer to Chart A, B, and C.

A. The title product of Example 5 (100 mg) is added to ethanol (4.5 ml) and cooled to −25° C. To the resulting mixture is added an ethanolic (8 ml) solution of thallium (III) nitrate trihydrate, TL $(ONO_2)_3.3H_2O$ (250 mg), dropwise over about 15 min. The resulting mixture is then stirred for 30 min at −25° C. and heated to reflux for 1-2 min. The reaction is then poured into saturated aqueous sodium bicarbonate and extracted with diethyl ether. The etheral layer is then dried over magnesium sulphate and concentrated under reduced pressure to yield formula XXXII product, 1-(6-hydroxy-4-ethoxy-7-methoxy-5-benzofuranyl)-ethanone.

B. To sodium hydride (20.1 g of a 50% dispersion in oil) and tetrahydrofuran (20 ml freshly distilled from lithium aluminum hydride), combined under a nitrogen atmosphere to form a slurry, are added dropwise a mixture of the product of Part A (56 g), ethyl 2-(methylthio)-acetate (26.4 g) and dry tetrahydrofuran (50 ml). After the addition is complete (1.5 hr) the reaction mixture is then heated on a steam bath for 15 min and cooled to ambient temperature. Thereupon excess sodium hydride is destroyed by careful addition of ice and water (300 ml). Washing with diethyl ether (600 ml) yields an aqueous layer which is diluted with methanol (100 ml) and concentrated hydrochloric acid (75 ml). This mixture is then refluxed for 45 min and thereupon allowed to cool to ambient temperature. Upon extraction with methylene chloride (600 ml) the organic extracts are dried and concentrated under reduced pressure to yield pure title product.

C. Alternatively title product is prepared as follows:
(1) 4,7-Dimethoxy-7-[(methylthio)methyl]-furochromone (15 g) is added to trichloromethane (250 ml). Anhydrous hydrobromic acid is then bubbled through the resulting mixture until a dark red color develops. The reaction is then heated to reflux for 45 min, cooled to ambient temperature, and diluted with water (200 ml). The organic layer is then separated, dried over magnesium sulphate, and concentrated under reduced pressure to yield 13.36 g of 4-hydroxy-7-[(methylthio)methyl]-9-methoxy-furochromone. Melting point 134°–135° C.

(2) The product of part C(1) (4.0 g) is added to acetone (100 ml), ethyl iodide (15 ml) and potassium carbonate (9 g). The resulting mixture is then heated to reflux for 18 hr, cooled to ambient temperature, and concentrated under reduced pressure. The resulting solid is then washed with trichloromethane and separated by filtration. Concentration under reduced pressure yields a dark oil which is chromatographed on 300 gr of silica gel by high pressure liquid chromatography. Packing in elution with 10% ethyl acetate in trichloromethane yields 3.0 g of title product, melting point 112°–114° C. Silica gel TLC Rf is 0.78 in 1% methanol in ethyl acetate. IR absorptions (cm$^{-1}$) are observed at 3120, 1650, 1610, 1380, 1340, 1210, 1170, and 1065. NMR absorptions are observed at 7.62, 6.97, 6.15, 4.21, 4.20, 4.57, and 2.21 δ.

FORMULAS

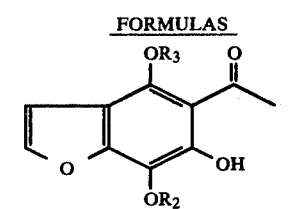

I

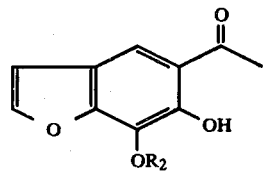

II

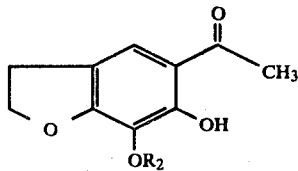

III

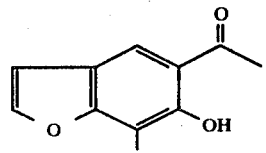

IV

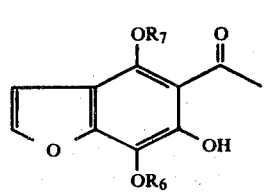

V

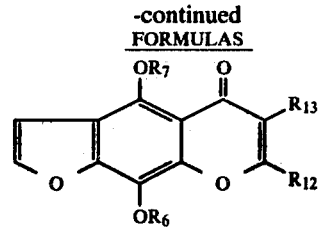

VI

CHART A

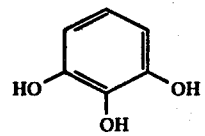

XXI

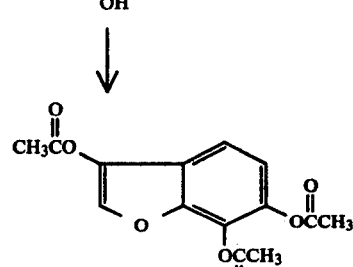

XXII

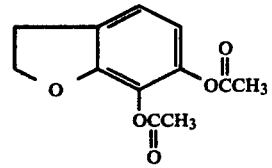

XXIII

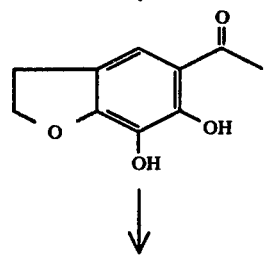

XXIV

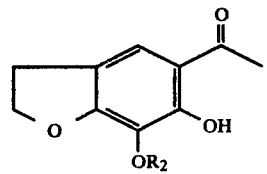

XXV

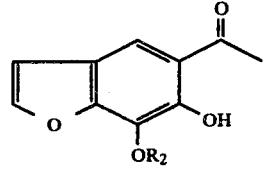

XXVI

CHART B

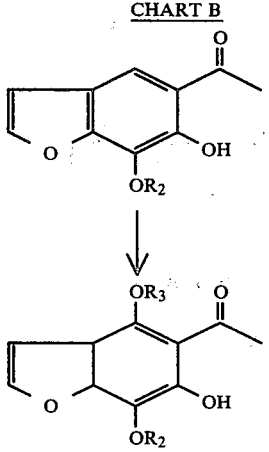

CHART C

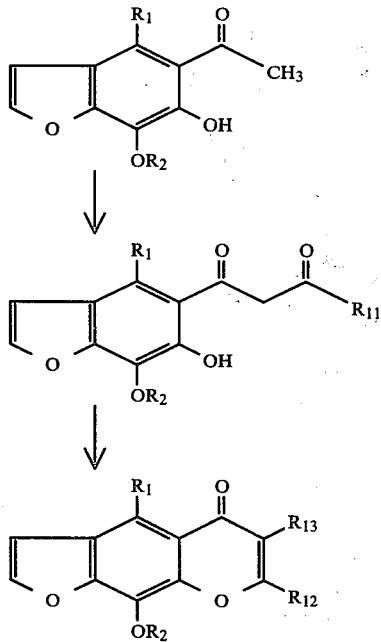

I claim:
1. A dihydrofuorochormone of formula I:

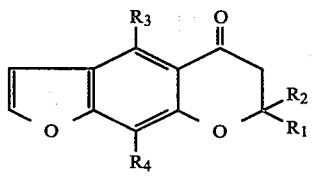

wherein $R_1$ and $R_2$, being the same or different, are individually:
(a) $C_1-C_6$ alkyl,
(b) trifluoromethyl,
(c) $C_5-C_{10}$ cycloalkyl with the proviso that the cycloalkyl ring is $C_5-C_7$,
(d) $C_2-C_8$ alkylaminoalkyl,
(e) $C_2-C_8$ alkoxyalkyl,
(f) $C_2-C_8$ alkylthioalkyl,
(g) $C_2-C_8$ alkylsulfinylalkyl,
(h) $C_2-C_8$ alkylsulfonylalkyl,
(i) $C_7-C_{12}$ phenoxyalkyl optionally substituted on the phenyl ring by one, 2, or 3,
  (i) hydroxy,
  (ii) $C_1-C_3$ alkoxy,
  (iii) $C_1-C_3$ alkyl,
  iv) trifluoromethyl,
  (v) halo which is fluoro, chloro, or bromo, with the proviso that no more than two such substituents are other than alkyl,
(j) $C_7-C_{12}$ phenylthioalkyl optionally substituted on the phenyl ring by one, 2, or 3,
  (i) hydroxy,
  (ii) $C_1-C_3$ alkoxy,
  (iii) $C_1-C_3$ alkyl,
  (iv) trifluoromethyl,
  (v) halo which is fluoro, chloro, or bromo, with the proviso that not more than two such substituents are other than alkyl,
(i) phenyl optionally substituted by one, 2, or 3,
  (i) hydroxy,
  (ii) $C_1-C_3$ alkoxy,
  (iii) $C_1-C_3$ alkyl,
  (iv) trifluoromethyl,
  (v) halo which is fluoro, chloro, or bromo, with the
(l) $C_7-C_{12}$ aralkyl optionally substituted on the aromatic ring by one, 2, or 3,
  (i) hydroxy,
  (ii) $C_1-C_3$ alkoxy,
  (iii) $C_1-C_3$ alkyl,
  (iv) trifluoromethyl,
  (v) halo which is fluoro, chloro, or bromo, with the proviso that not more than two such substituents are other than alkyl,
(m) 2- or 3-furanyl optionally substituted by
  (i) hydroxy,
  (ii) $C_1-C_3$ alkoxy,
  (iii) $C_1-C_3$ alkyl,
  (iv) trifluoromethyl,
  (v) halo which is fluoro, chloro, or bromo, with the proviso that not more than two such substituents are other than alkyl,
(n) 2- or 3-thenyl optionally substituted by
  (i) hydroxy,
  (ii) $C_1-C_3$ alkoxy,
  (iii) $C_1-C_3$ alkyl,
  (iv) trifluoromethyl,
  (v) halo which is fluoro, chloro, or bromo, with the proviso that not more than two such substituents are other than alkyl, or
(o) $-CH_2NR_8R_9$ wherein $R_8$ and $R_9$, being the same or different, are individually,
  (i) hydrogen,
  (ii) $C_1-C_8$ alkyl,
  (iii) $C_5-C_{10}$ cycloalkyl,
  (iv) $C_7-C_{12}$ aralkyl, or
  (v) phenyl optionally substituted by one, 2, or 3
    (a) hydroxy,
    (b) $C_1-C_3$ alkoxy,
    (c) $C_1-C_3$ alkyl,
    (d) trifluoromethyl,
    (e) halo which is fluoro, chloro, or bromo, with the proviso that not more than two such substituents are other than alkyl, or wherein $R_8$ and $R_9$ are taken together with the nitrogen to form a saturated or unsaturated heterocyclic amine ring selected from the group consisting of thiazolidine, 3-piperidine methanol, 2-piperidine methanol, 3-piperidine ethanol, 2-piperidine ethanol, 1-piperizinepropanol, 4-phenyl-1,2,3,6-tetrahydropyridine, 4-phenylpiperidine, proline, 3-pyrolidinol, tetrahydrofurfurylamine, 3-pyrroline, thiazolidine-4-carboxylic acid, thiomorpholine, morpholine, 2-methylpiperidine, 3-methylpiperidine, 4-methylpiperidine, N-methylpiperazine, and 1-methylhomopiperazine, said heterocyclic amine ring being optionally substituted by $C_1$–$C_4$ alkyl, $C_2$–$C_8$ alkylthiomethyl, $C_2$–$C_8$ alkoxymethyl, $C_1$–$C_4$ hydroxymethyl or phenyl; or wherein $R_1$ and $R_2$ are taken together and form a bivalent moiety which is:
(a) —$CH_2$—$(CH_2)_a$—$CH_2$— wherein the integer "a" is zero to 5;
(b) —$CH_2$—$(CH_2)_b$—X—$(CH_2)_c$—$CH_2$—
wherein the integer "b" is zero and the integer "c" is zero, one, 2, or 3 or the integer "b" is one and the integer "c" is zero, one, or 2, and wherein X is oxa (—O—), thia (—S—), or —$N(R_{10})$— wherein $R_{10}$ is
  (i) hydrogen,
  (ii) $C_1$–$C_8$ alkyl,
  (iii) $C_5$–$C_{10}$ cycloalkyl,
  (iv) $C_7$–$C_{12}$ aralkyl, or
  (v) phenyl optionally substituted by one, 2, or 3
    (a) hydroxy,
    (b) $C_1$–$C_3$ alkoxy,
    (c) $C_1$–$C_3$ alkyl,
    (d) trifluoromethyl,
    (e) halo which is fluoro, chloro, or bromo, with the proviso that not more than two such substituents are other than alkyl;
wherein $R_3$ is hydrogen, or $C_1$–$C_4$ alkoxy and $R_4$ is hydrogen or $C_1$–$C_4$ alkoxy, with the provisos that one of $R_3$ and $R_4$ is hydrogen only when the other is other than hydrogen and $R_3$ and $R_4$ are the same or different.

2. 6,7-Dihydro-4,9-dimethoxy-7,7-dimethyl-5H-furo[3,2-g][1]benzopyran-5-one, a dihydrofurochromone according to claim 1.

3. 7-Ethyl-6,7-dihydro-4,9-dimethoxy-7-methyl-5H-furo[3,2-g][1]benzopyran-5-one, a dihydrofurochromone according to claim 1.

4. 7,7-Diethyl-6,7-dihydro-4,9-dimethoxy-5H-furo[3,2-g][1]benzopyran-5-one, a dihydrofurochromone according to claim 1.

5. 6,7-Dihydro-4,9-dimethoxy-7-methyl-7-phenyl-5H-furo[3,2-g][1]benzopyran-5-one, a dihydrofurochromone according to claim 1.

6. 4',9'-Dimethoxy-spiro[cyclopentane-1,7'-[7H]furo[3,2-g][1]benzopyran]-5'(6'H)-one, a dihydrofurochromone according to claim 1.

7. 4',9'-Dimethoxy-spiro[cyclohexane-1,7'-[7H]furo[3,2-g][1]benzopyran]-5'(6'H)-one, a dihydrofurochromone according to claim 1.

8. 2',3',5',6'-Tetrahydro-4,9-dimethoxy-spiro[7H-furo[3,2-g][1]benzopyran-7,4'-[4H]thiopyran]-5(6H)-one, a dihydrofurochromone according to claim 1.

9. 2',3',5',6'-Tetrahydro-4,9-dimethoxy-spiro[7H-furo[3,2-g][1]benzopyran-7,4'-[4H]thiopyran]-5(6H)-one, 1'-oxide, a dihydrofurochromone according to claim 1.

10. 2',3',5',6'-Tetrahydro-4,9-dimethoxy-spiro[7H-furo[3,2-g][1]benzopyran-7,4'-[4H]thiopyran]-5(6H)-one, 1',1'-dioxide, a dihydrofurochromone according to claim 1.

11. 6,7-Dihydro-4,9-dimethoxy-7-methyl-7-[(methylthio)methyl]-5H-furo[3,2-g][1]benzopyran-5-one, a dihydrofurochromone according to claim 1.

12. 6,7-Dihydro-4,9-dimethoxy-7-methyl-7-[(methylthio)methyl]-5H-furo[3,2-g][1]benzopyran-5-one, oxide, a dihydrofurochromone according to claim 1.

13. 6,7-Dihydro-4,9-dimethoxy-7-methyl-7-[(methylthio)methyl]-5H-furo[3,2-g][1]benzopyran-5-one, dioxide, a dihydrofurochromone according to claim 1.

14. 4,9-Dimethoxy-1'-methyl-spiro[7H-furo[3,2-g][1]benzopyran-7,4'-piperidine]-5(6H)-one, a dihydrofurochromone according to claim 1.

* * * * *

UNITED STATES PATENT AND TRADEMARK OFFICE
CERTIFICATE OF CORRECTION

PATENT NO. : 4,434,295  Page 1 of 2
DATED : February 28, 1984
INVENTOR(S) : Ronald B. Gammill It is certified that error appears in the above-identified patent and that said Letters Patent is hereby corrected as shown below: Item [56] :

Front Page (Other Publications, Column 2), "Schur" should read -- Schurr --.
Column 2, line 12, "1806α7" should read -- 1806-7 --.
Column 6, line 5, "$C_2 14 \ C_8$" should read -- $C_2-C_8$ --.
Column 9, line 40, "$(cm^-)$" should read -- $(cm^{-1})$ --.
Column 9, line 66, "$(cm^-)$" should read -- $(cm^{-1})$ --.
Column 11, line 13, "0.1 L in" should read -- 0.1 in --.
Column 14, line 9, "Chim. Intal.," should read -- Chim. Ital., 88:910 (1958). --
Column 20, line 66, "yield a reaction." should read -- yield a residue. --.
Column 25, line 48, "dimetoxyfurochromone" should read -- dimethoxyfurochromone --.
Column 25, line 59, "Stath" should read -- Spath --.
Column 27, line 43, "dimetoxyfurochromones." should read -- dimethoxyfurochromones. --.
Column 31, line 24, "Exaple" should read -- Example --.

UNITED STATES PATENT AND TRADEMARK OFFICE
CERTIFICATE OF CORRECTION

PATENT NO. : 4,434,295

DATED : February 28, 1984

INVENTOR(S) : Ronald B. Gammill

It is certified that error appears in the above-identified patent and that said Letters Patent is hereby corrected as shown below:

Column 36, line 21, claim 1, "(i)" should read -- (k) --.

Signed and Sealed this

Thirtieth Day of April 1985

[SEAL]

Attest:

DONALD J. QUIGG

Attesting Officer  Acting Commissioner of Patents and Trademarks